United States Patent
Blackwell et al.

(10) Patent No.: US 12,293,819 B2
(45) Date of Patent: May 6, 2025

(54) COMPUTER-IMPLEMENTED METHOD FOR PROVIDING CARE

(71) Applicant: IESO Digital Health Limited, Cambridge (GB)

(72) Inventors: Andrew Blackwell, Cambridge (GB); Danah Tangen, Cambridge (GB); Michael Ewbank, Cambridge (GB); Thomas Fabian James Clelford, Cambridge (GB); Mihai Valentin Tablan, Cambridge (GB); Jennifer Gentile, Cambridge (GB); Sabine Nicole Buchholz, Cambridge (GB); Stephen Freer, Cambridge (GB); Ana Maria Ferreira Paradela Catarino Wingfield, Cambridge (GB); Ronan Patrick Cummins, Cambridge (GB); Shaun Mehew, Cambridge (GB); Emily Marshall, Cambridge (GB)

(73) Assignee: IESO DIGITAL HEALTH LIMITED, Cambridge (GB)

( * ) Notice: Subject to any disclaimer, the term of this patent is extended or adjusted under 35 U.S.C. 154(b) by 0 days.

(21) Appl. No.: 17/995,913

(22) PCT Filed: Jun. 24, 2022

(86) PCT No.: PCT/GB2022/051629
§ 371 (c)(1),
(2) Date: Oct. 10, 2022

(87) PCT Pub. No.: WO2022/269286
PCT Pub. Date: Dec. 29, 2022

(65) Prior Publication Data
US 2024/0221908 A1 Jul. 4, 2024

(30) Foreign Application Priority Data

Jun. 25, 2021 (GB) ..................................... 2109185
Mar. 25, 2022 (GB) ..................................... 2204282

(51) Int. Cl.
*G16H 20/70* (2018.01)
*G06F 40/35* (2020.01)
(Continued)

(52) U.S. Cl.
CPC ............. *G16H 20/70* (2018.01); *G06F 40/35* (2020.01); *G16H 10/20* (2018.01); *G16H 50/30* (2018.01)

(58) Field of Classification Search
CPC .......... G06F 40/35; G06F 40/30; G06F 40/56; G16H 20/70; G16H 10/20; G16H 50/30
See application file for complete search history.

(56) References Cited

U.S. PATENT DOCUMENTS 10,817,787 B1    10/2020  Zhang
11,631,401 B1 *   4/2023  Nudd ..................... G16H 80/00
                                                                 704/9
(Continued)

FOREIGN PATENT DOCUMENTS

CN      108920510 A    11/2018
KR      20210058449 A   5/2021
WO      2020036467 A1   2/2020

OTHER PUBLICATIONS

International Search Report and Written Opinion for corresponding PCT Application No. PCT/GB2022/051629 mailed Sep. 27, 2022.
(Continued)

*Primary Examiner* — Stella L. Woo
(74) *Attorney, Agent, or Firm* — ALSTON & BIRD LLP

(57) ABSTRACT

A conversational agent is provided for maintaining or improving the wellbeing of a user presenting with mental
(Continued)

health needs by the delivery of a care protocol. The conversational agent comprises: a plurality of sub-dialogue units, each configured to deliver an element of the care protocol, and an orchestrator configured to present the sub-dialogue units to the user, sequentially, wherein each sub-dialogue unit and the orchestrator comprises: a natural language understanding module configured to receive an input and/or reply and determine at least one intent and, where present, at least one slot within the input and/or reply; a dialogue planning module configured to determine an output based, at least in part, on the at least one intent and/or slot associated within the input and/or reply, and a natural language generation module configured to provide the output to the user.

16 Claims, 11 Drawing Sheets

(51) Int. Cl.
*G16H 10/20* (2018.01)
*G16H 50/30* (2018.01)

(56) References Cited

U.S. PATENT DOCUMENTS

| | | |
|---|---|---|
| 11,763,919 B1* | 9/2023 | Jain ..................... G16H 40/63 715/221 |
| 2015/0099257 A1 | 4/2015 | Kozloski et al. |
| 2016/0140320 A1* | 5/2016 | Moturu ................. G09B 7/06 434/236 |
| 2017/0324868 A1 | 11/2017 | Tamblyn et al. |
| 2020/0302952 A1 | 9/2020 | Pinkus et al. |
| 2021/0098110 A1* | 4/2021 | Periyasamy ........... G16H 20/70 |
| 2021/0134179 A1 | 5/2021 | Zilca et al. |
| 2021/0272585 A1 | 9/2021 | Han et al. |
| 2021/0335498 A1* | 10/2021 | Kulkarni ................ G16H 50/20 |
| 2022/0068462 A1* | 3/2022 | Dolan .................... G10L 25/63 |
| 2022/0223259 A1* | 7/2022 | Bergh .................... G16H 50/20 |
| 2022/0310246 A1* | 9/2022 | Larsen ................... G16H 10/20 |
| 2022/0353209 A1* | 11/2022 | Yannam ............ G06F 16/24565 |
| 2023/0353512 A1* | 11/2023 | Gollareddy ............. G06F 3/167 |

OTHER PUBLICATIONS

Search report of the priority application completed on Nov. 23, 2021.

* cited by examiner

COMPUTER-IMPLEMENTED METHOD FOR PROVIDING CARE

The present invention relates to computer-implemented methods for providing care and, more specifically, to computer-implemented methods for maintaining or improving a user's state of wellbeing.

Voice-driven computing and artificial intelligence is becoming more and more pervasive in our lives, supported by the presence and integration of such technology on our phones, appliances and in our cars. In coming years, talking to a computer, via text or voice, will increasingly be how many of us perform a growing number of activities. The awareness of an individual's state of well-being is also on the rise. Consequently, provisions for providing support, coaching, treatment and/or therapy are of interest.

These voice-driven computing systems are typically relatively uncomplex. The complexity of a bot running an interactive system may be measured in "turns"—i.e. the number of interactions between the bot and the user required to complete the activity. A bot that enables a user to, for example, check the weather forecast for a given location or confirm the timing of their next medication, may require between one and ten turns, for example.

In contrast, psychotherapy interactions are complex. In patient-therapist text-based cognitive behavioural therapy (CBT), a patient will typically spend around 6 hours in therapy sessions in which the CBT protocol is delivered. There will be, on average, around 50 "turns" per hour and therefore the system will need to handle of the order of several hundred turns. Other protocols, including specific forms of CBT protocols, may also be delivered. These protocols may be deemed 'care protocols'.

It is against this background that the present invention has arisen.

According to the present invention there is provided a conversational agent for maintaining or improving the wellbeing of a user presenting with mental health needs by the delivery of a care protocol, the conversational agent comprising: a plurality of sub-dialogue units, each configured to deliver an element of the care protocol; and an orchestrator configured to present the sub-dialogue units to the user, sequentially, wherein each sub-dialogue unit and the orchestrator comprises: a natural language understanding module configured to receive an input and/or reply and determine at least one intent and, where present, at least one slot within the input and/or reply; a dialogue planning module configured to determine an output based, at least in part, on the at least one intent and/or slot associated within the input and/or reply, and a natural language generation module configured to provide the output to the user. The division of the conversational agent into a number of different "sub-dialogue units" is intended to address the complex requirements of psychotherapy interactions. As such, the overall conversation, or dialogue, may be divided into a number of different stages, or sub-dialogues, wherein each stage, or sub-dialogue, is delivered by a separate sub-dialogue unit.

There may be three, five, six, eight, ten, twenty, thirty or more sub-dialogue units. Each sub-dialogue unit has a specific function to deliver an element of a care protocol, for example a CBT protocol. Each sub-dialogue unit comprises a natural language understanding module, a dialogue planning module and a natural language generation module. The sub-dialogue units together constitute a conversational agent capable of guiding a patient through a care protocol. There may be a number of different variants of a sub-dialogue unit intended to deliver a specific element of a care protocol. For example, different variants of a sub-dialogue unit may be configured to be appropriate for different severities of a condition.

More specifically, each natural language understanding module may be configured to identify, if present within the input and/or reply, at least one intent from a list of predetermined intents associated with the corresponding sub-dialogue unit.

The division of the care protocol into a number of different elements of care, each delivered by a dedicated sub-dialogue unit, makes each sub-dialogue unit more accurate and efficient as it works with a lower number of intents, for example, between six and ten intents. However, the division into sub-dialogues, in turn, necessitates the management of the overall psychotherapy interaction. This management is provided by an orchestrator which introduces each sub-dialogue unit to the user and then steps in between each subsequent sub-dialogue unit to provide a bridge between the sub-dialogues, thus providing the user with a more engaging and natural conversation.

The orchestrator is configured as a sub-dialogue unit comprising a natural language understanding module, a dialogue planning module and a natural language generation module. In particular, the orchestrator natural language understanding module may be configured to receive an input and/or reply and determine at least one intent and, where present, at least one slot within the input and/or reply. The identified intent may be from a list of predetermined intents associated with the orchestrator sub-dialogue unit. The orchestrator dialogue planning module may be configured to determine an output based, at least in part, on the at least one intent and/or slot associated within the input and/or reply received by the orchestrator natural language understanding module. The orchestrator natural language generation module may be configured to provide the output determined by the orchestrator dialogue planning module to the user. The aim of the orchestrator is not to deliver an element of a care protocol, but to enhance the user's experience and increase or maintain their level of engagement with the psychotherapy. The conversational nature of the agent, delivered with the use of the orchestrator, gives the user an experience that is intended to mirror more closely interactions with a human therapist with the intention of keeping the level of engagement to a higher level than can typically be achieved by App based delivery.

The care protocol may be a clinical protocol, for example a psychotherapy protocol. The protocol may be a CBT protocol, for example a transdiagnostic CBT protocol.

The conversational agent may comprise in excess of ten sub-dialogue units. Alternatively, the conversational agent may comprise in excess of 20 sub-dialogue units or 30 sub-dialogue units. The selection of the number of sub-dialogue units is influenced by the order of magnitude of the number of turns required to deliver the protocol. The number of sub-dialogue units is selected in order to keep the number of intents that each sub-dialogue unit has to manage to a reasonable level. For example, the number of sub-dialogue units may be selected to ensure that the number of intents that each sub-dialogue unit has to manage is in the range of six to ten and does not exceed 20. The number of intents that each sub-dialogue unit has to manage may be represented by the predetermined list of intents associated with that sub-dialogue unit.

The orchestrator may be configured to select which sub-dialogue unit is presented to the user. This provides an advantage over systems where the ordering of the sub-dialogue units is fixed because it allows for the delivery of the care protocol to be personalized for the user during its delivery. For example, on the basis of performance within a sub-dialogue unit, the orchestrator may be configured to present a different sub-dialogue unit to the user from that which had been originally intended to follow the currently active sub-dialogue unit. In one embodiment, if, during an initial "assessment" sub-dialogue, there had been no mention of "sleep disruption" then the care protocol as originally formulated would not have included the "sleep disruption" sub-dialogue unit. However, if, during a different sub-dialogue, the user makes several mentions of sleep disruption, then the orchestrator may be configured to amend the care protocol in order to present the "sleep disruption" sub-dialogue unit to the user.

The orchestrator may also manage the order in which a user interacts with the sub-dialogue units. For example, a user may commence with an "onboard" sub-dialogue and may then pass to a subsequent "assessment" sub-dialogue unit. Subsequent sub-dialogue units may include other elements of a CBT protocol such as "values" and "perspective taking." The order in which the sub-dialogue units are presented to the user is managed by the orchestrator including, if deemed appropriate, repeating some sub-dialogues before moving onto a new sub-dialogue or even reverting to a sub-dialogue unit completed initially at an early stage in the process, but revisited for greater perspective after completing various other sub-dialogues. The orchestrator will also select the variant of sub-dialogue unit that is appropriate for a user where a sub-dialogue unit has more than one variant associated with a different level of severity of assessed state of wellbeing. The orchestrator also manages the closure of a session of therapy, managing the user's expectations and optimising their ongoing engagement with the process.

The conversational agent may further comprise a risk assessment sub-dialogue unit which comprises a natural language understanding module configured to receive an input and/or reply for a user and analyse the input to determine at least one intent and, where present, at least one slot within the input and/or reply. The risk assessment sub-dialogue unit may be configured to receive and analyse all inputs from the user. The risk assessment sub-dialogue unit may further comprise a dialogue planning module configured to determine an output based, at least in part, on the at least one intent and/or slot associated within the input and/or reply, and a natural language generation module configured to provide the output to the user. The risk assessment sub-dialogue unit may be configured to identify whether one or more intents identified in each user input and/or reply correspond to a predetermined list of intents associated with risk. Therefore, the natural language understanding module of the risk assessment sub-dialogue unit may be configured to receive an input and/or reply from a user and, if present within the input and/or reply, identify an intent indicating a risk.

The provision of a sub-dialogue unit that is devoted to monitoring for intents indicative of risk means that each of the care protocol sub-dialogue units does not need to carry this functionality. The risk sub-dialogue unit, by receiving and analysing all inputs from the user, acts in the background, listening to all inputs from the user. This means that the risk sub-dialogue unit is running in parallel to an active sub-dialogue unit with which a user is engaged.

The conversational agent may further comprise an adjudicator configured to identify each sub-dialogue unit comprising a natural language understanding module that identifies an intent; determine which of the identified sub-dialogue units meets a predetermined criterion; and select the sub-dialogue unit that meets the predetermined criterion such that only the selected sub-dialogue unit determines and provides an output to the user in response to each input. The role of the adjudicator is to determine priority between multiple sub-dialogue units, so it is external to the sub-dialogue units themselves.

The adjudicator may be configured to enable the risk assessment sub-dialogue unit to provide an output to the user, where an intent relating to risk is identified. This effectively enables the risk sub-dialogue unit to interrupt the flow of the delivery of the care protocol overall as a result of an identification of risk.

The computer-based system may be configured to receive and interpret an external assessment in addition to or in place of an "assessment" sub-dialogue unit. If an external, for example General Practitioner (GP) led, assessment is provided, this GP led assessment may be used to adapt or direct the variant of the "assessment" sub-dialogue unit that is deployed in the user's care protocol. The "assessment" sub-dialogue unit can be used to verify and/or augment the external assessment. For example, if the user has previously completed a GAD-7 assessment with their GP and the results of this have been provided to the system then the "assessment" sub-dialogue unit may present a GAD-2 diagnostic questionnaire and, provided there is sufficient correlation between the GAD-2 and the GP led GAD-7 assessment, then the "assessment" sub-dialogue can complete on this basis. This is a further example of a dynamic adaptation of the system that encourages the user to engage with the system. In the absence of this flexibility, the user could be demotivated by feeling that they had to revisit matters that had already been fully addressed by their GP within the care protocol. The ability to modify the care protocol appropriately may enhance engagement.

According to the present invention there is provided a computer-implemented method for maintaining or improving the wellbeing of a user presenting with mental health needs, the method comprising: receiving an input from a user; analysing the input using a natural language understanding module configured to determine at least one intent and, where present, at least one slot within the input; determining an output using a dialogue planning module, wherein the output is based, at least in part, on the at least one intent and/or slot associated with the input; providing the output to the user using a natural language generation module; and receiving, in response to the output, a reply from the user.

More specifically, there may be provided a sub-dialogue unit for maintaining or improving the wellbeing of a user presenting with mental health needs. Each sub-dialogue unit may be configured to carry out the aforementioned method. There may also be provided a conversational agent comprising a plurality of sub-dialogue units. Again, each sub-dialogue unit in the conversational agent may be configured to carry out the aforementioned method.

A user's mental health needs may comprise a diagnosis of generalized anxiety disorder (GAD), anxiety and/or depression. Furthermore, a user's mental health needs may comprise a sub-clinical level of anxiety which may not reach a clinical threshold.

A user's state of wellbeing may comprise their physical, mental and/or social wellbeing. Alternatively, or additionally, a user's state of wellbeing may comprise their emotional, psychological, spiritual, educational and/or intellectual wellbeing. More specifically, a user's mental and/or emotional wellbeing may comprise a user's state of stress.

A user's state of wellbeing may be measured using any suitably validated self-assessment questionnaire, including, but not limited to at least one of a: Patient Health Questionnaire (PHQ-9); Generalised Anxiety Disorder Assessment (GAD-7); and/or Patient Activation Measure (PAM).

The PHQ-9 is a measure of depressive symptoms, ranging from 0 to 27, with higher scores representing greater depression severity. The GAD-7 is a measure of anxiety symptoms, ranging from 0 to 21, with higher scores representing higher anxiety severity.

The PAM questionnaire returns a total score, and a PAM level. The total score is a continuous variable, ranging from 0 to 100 with 100 representing maximum patient engagement with the management of their physical health condition. The PAM level is an ordinal variable with 4 levels, with higher levels representing better patient engagement with the management of their physical health condition: Level 1—"Disengaged and Overwhelmed"; Level 2—"Becoming Aware, But still Struggling", Level 3—"Taking Action", Level 4—"Maintaining Behaviours and Pushing Further".

The computer-implemented method may provide at least of one of support, coaching, treatment and/or therapy. The treatment may comprise stress management. The therapy may be psychotherapy. The psychotherapy may be provided as a clinical level intervention. Alternatively, or in addition, the therapy may be preventative therapy. Preventative therapy may be appropriate for an individual previously identified as being at risk, during a pre-clinical phase. For example, the computer-implemented method, when provided as preventative therapy, may be configured to prevent the worsening of a user's symptoms.

Psychotherapy may comprise preventative therapy, intervention therapy and/or coaching. For example, the computer-implemented method may provide psychotherapy, this resulting in a user receiving protection, prevention and/or treatment measures relating to their wellbeing and, in particular, their mental wellbeing. Each of the aforementioned treatment measure may be within the context of care. Psychotherapy may comprise Cognitive Behavioral Therapy (CBT) and/or Acceptance and Commitment Therapy (ACT).

In some embodiments, the computer-implemented method may provide psychotherapy for treating common mental health conditions, such as depression and/or anxiety disorders. Alternatively, or in addition, the computer-implemented method may determine, monitor and/or improve a user's wellbeing.

Determining an output based, at least in part, on the intent and/or slot associated with the input enables the exchange between the computer system and the user to be more conversational, thus improving user engagement and, consequently, the likelihood of successfully maintaining or improving a user's state of wellbeing.

In some embodiments, the entirety of the output may be determined based on the intent and/or slot associated with the input. Determining the entirely of the output based on the at least one intent/or slot associated with the input ensures that the entirety of the output is configured to best respond to the user input. This prevents a predetermined output, or a predetermined component thereof, from being forced upon the user, which may in turn decrease the user engagement level.

The reply may be the input for a subsequent iteration of the method. In other words, the input may be a previous reply. The reply may be based, at least in part, on the output. In some embodiments, the user may be a patient.

The natural language understanding module, dialogue planning module and natural language generation module may form part of a conversational agent. For example, the conversational agents may be an entity comprising artificial intelligence (AI) capable of holding a conversation. Alternatively, or additionally, in order to manage complex conversations, in some embodiments the conversational agent may be composed of multiple sub-dialogues. Each sub-dialogue may be formed from a natural language understanding module, a dialogue planning module and a natural language generation module.

The input may comprise an utterance. Alternatively, or in addition, the input may comprise audio, text and/or a picture. The input may comprise an emotion icon (emoticon) or emoji. The method may comprise converting the input into text.

The intent may be: provide a trigger and/or provide a symptom. Alternatively, or in addition, the intent may be: greet, goodbye, affirm, deny, inform thought, inform sensation, inform emotion and/or inform behaviour.

The intent may be used to predict the purpose of the input. For example, if an input comprises "I got really agitated last week as I was driving to work because I was worried I hadn't locked the door." The intent may be "provide a trigger". This may be in response to a previous output from the natural language generation module. However, the input may comprise a plurality of intents. For example, the input may comprise 1, 2, 3, 4, 5, 6, 7, 8, 9, 10 or more than 10 intents.

In some embodiments, the, or each, natural language understanding module may be configured to identify, if present within the input and/or reply, at least one intent from a list of predetermined intents associated with the corresponding sub-dialogue unit.

The slot may be: a symptom, an occurrence, a time, a date, a trigger, and/or a situation. Alternatively, or in addition, the slot may be: a thought, a sensation, an emotion, a behaviour and/or a feeling.

A slot may be one or more semantic concepts. For example, in the previous example, the slots may comprise: "situation: driving to work" and "trigger: I was worried I hadn't locked the door". However, any number of slots may be present in an input. For example, the input may comprise 0, 1, 2, 3, 4, 5, 6, 7, 8, 9, 10 or more than 10 slots.

The method may further comprise: determining a user engagement level, wherein the output is based, at least in part, on the user engagement level. Determining a user's engagement level and adapting the output based on the user engagement level enables a predetermined user engagement level to be maintained. For example, the output may be based, at least in part, on the need to increase the user's engagement level. This increases the likelihood of the user engaging with the computer-implemented method for an adequate amount of time, thus increasing the likelihood of maintaining or improving a user's state of wellbeing.

In some embodiments, the predetermined user engagement level may be achieved if the user sends a second input. The second input may be the reply. The output may be configured to increase the likelihood of the user sending a second input. For example, the output may comprise a list of options from which the user may select a second input and/or reply. Alternatively, or in addition, the output may comprise a task or a game.

Alternatively, the predetermined user engagement level may be achieved if the user provides a predetermined intent and/or slot or a predetermined number of intents and/or slots. The predetermined intent and/or slot or a predetermined number of intents and/or slots may be provided in the reply and/or in a subsequent input. The output may be configured to increase the likelihood of the user sending the predetermined intent and/or slot. For example, the output may comprise a question.

The predetermined user engagement level may vary between the input and reply. Similarly, the predetermined user engagement level may vary between a user's first and second input. Alternatively, or in addition, the predetermined user engagement level may vary between a first and second user. The output may be personalized. More specifically, the output style, form and/or content may be personalized. For example, the output style, form and/or content may be based on a user's condition and/or symptom state.

The user engagement level may be determined based on the input. The input may be a reply from a previous cycle of the method. More specifically, the user engagement level may be determined based on at least one characteristic of the input. For example, the user engagement level may be determined based on the content and/or quantity of the intent(s) and/or slot(s). Alternatively, or in addition, the user engagement level may be determined based on at least one of the language, tone, spelling, grammar and punctuation within the input. However, any characteristic of the input, or absence thereof, may be used to determine user engagement level.

Alternatively, or in addition, the user engagement level may be determined based on a previous input. The previous input may be a previous reply. The previous input may be the user's immediately previous input or any input generated by the user in the past. The previous input may be stored in a dialogue history module. The previous input may be associated with a corresponding event. An event may comprise a corresponding input, output and/or reply. The event may further comprise a second input, output or reply. The event may also comprise the absence of a second input. Similarly, the event may comprise the absence of a reply. The user engagement level may be predicted based on a previous event.

The previous event may relate to a second user. There may be any number of second users. The second user may be another user, in addition to the first user, seeking to maintain or improve their state of wellbeing. For example, the second user may be a different user within a group therapy session comprising the first user. Alternatively, or in addition, the second user may be a user seeking to maintain or improve their state of wellbeing in isolation. Moreover, the second user may be a therapist, human care provider, family member of the first user, relative of the first user or friend of the first user.

A family member may be an extended family member. For example, the user's family members may comprise a spouse, partner, sibling, parent, grandparent, grandchild, cousin, aunt, uncle, step-parent or step-sibling. A family member may also be a foster family member or an adopted family member.

The user engagement level may be determined based on a plurality of previous events. The plurality of previous events may relate to a plurality of different users. In some embodiments, a neural network may be used to determine the user engagement level. Alternatively, or in addition, a statistical model may be used to determine the user engagement level. The user engagement level may be determined based on the probability of a given event occurring. For example, the user engagement level may be determined based on the probability of a user providing a second input.

The user engagement level may be determined at predetermined time intervals. For example, the user engagement level may be determined every second, every minute, every hour or every day. Alternatively, or in addition, the user engagement level may be determined upon receipt of an input. The user engagement level may be continuously monitored. The user engagement level may be monitored digitally and/or by a second user. Alternatively, or in addition, the user engagement level may be periodically reviewed. The user engagement level may be reviewed digitally and/or by a second user.

The method may further comprise: determining if the user engagement level is below a predetermined threshold; and sending an alert to a second user upon determining a user engagement level below the predetermined threshold. Accordingly, upon determining a user engagement level below a predetermined threshold, an alert may be sent to a human care provider. Alerting a second user when a user engagement level below a predetermined threshold is identified gives the second user the opportunity to prevent the first user engagement level from decreasing further. Moreover, the second user may ensure that the first user's engagement level does not remain below the predetermined engagement threshold.

The second user may be a family member of the first user, relative of the first user and/or friend of the first user. The alert may be configured to encourage the second user to enhance the user engagement level of the first user. For example, friends and/or family could be introduced into a conversation comprising the first user in order to maximise the user engagement level of the first user. Similarly, in a group treatment situation, the first user's peers may be sent an alert configured to encourage the second user to assist with increasing the user engagement level of the first user. For example, the alert may tell the second user that the first user is struggling. The alert may also suggest that the second user sends the first user an encouraging message. The second user may be the first user's friend, family member, or peer help-seeker.

The predetermined threshold may be a minimum threshold. In some embodiments, the user may stop engaging entirely at the minimum engagement threshold. Therefore, in some embodiments, the predetermined threshold is above the minimum threshold. The minimum threshold may be satisfied by receipt of a reply.

After having received the alert, the second user may provide a second output to the user. In some situations, the second user may be better suited to increase and/or maintain an engagement level above the predetermined threshold. Therefore, a bespoke output generated by the second user may increase the likelihood of maintaining or improving a user's state of wellbeing.

In some embodiments, the second output may be, at least in part, auto-generated. The second user may amend and/or supplement the auto-generated second output. In some embodiments, the second user may amend the second output by adding their name.

In some embodiments, the second output is intended to increase the user engagement level. The second output may be solely intended to increase the user engagement level.

Alternatively, or in addition, after having received the alert, the second user may amend the output determined by the dialogue planning module. As previously disclosed, the second user may be better suited to increase and/or maintain an engagement level above the predetermined threshold in a given situation. Allowing the second user to amend the output may increase the user engagement level, which, in turn, may increase the likelihood of maintaining or improving a user's state of wellbeing.

The method may further comprise: reviewing the second output and provided further amendments where needed. Alternatively, or in addition, the method may comprise: reviewing the amended output and provided further amendments where needed. The second output and/or amended output may be reviewed using the natural language understanding module. The second output and/or amended output may be further amended using the dialogue planning module. The further amendments may be corrections, such as spelling corrections. Alternatively, or in addition, the further amendments may prevent the user from receiving an unsuitable output. An "unsuitable" output may be an output that contradicts a previous output. Alternatively, or in addition, an "unsuitable" output may be an output that deviates from a predetermined treatment plan. Alternatively, or in addition, an "unsuitable" output may be an output that has previously resulted in the user's engagement falling below the predetermined engagement threshold.

Moreover, the system, and in particular the dialogue planning module, may learn from the amended output and adapt future outputs based on the amended output. This may help to decrease the likelihood of a user's engagement level falling below the predetermined threshold under the same, or similar, conditions in the future.

In some embodiments, after having received the alert, the second user generates a second output for providing to the user. The method may further comprise the step of reviewing the amended output and/or the second output and provided further amendments where needed.

In some embodiments, the method may be entirely autonomous. An entirely autonomous method, without the involvement of a second user, such as a human care provider, enables a larger number of users to simultaneously improve or maintain their state of wellbeing via the computer-implemented method. Accordingly, human care providers can focus on engaging with and/or providing treatment to users most in need at any given time. Furthermore, an autonomous computer system may be available 24 hours a day, thus enabling users to engage with the computer system whenever they need it.

The output may be determined using a combination of predetermined rules and statistical methods. Predetermined rules offer more control over the output and thus the most probable next input, but may be inflexible, leading to an output that is uninteresting, formulaic, and non-engaging. By contrast, statistical dialogue planners tend to be more flexible, leading to a more human-like output, but may be harder to control, and may make mistakes that are more difficult to fix.

Therefore, determining the output using a combination of predetermined rules and statistical methods enables the output to utilise the best of each method, thus increasing the likelihood of providing successful psychotherapy and/or treatment in addition to providing a more natural-sounding output.

For example, administering a questionnaire (in dialogue form) may be best handled by a simple rule-based plan, while a complex dialogue, such as doing formulation during the user assessment may best be implemented statistically.

The method may comprise: reviewing a memory configured to store at least one event, wherein each event comprises: an intent and, where present, at least one slot corresponding to a previous input; a previous output corresponding to the previous input, and where present, a second previous input received subsequent to the previous output, wherein the output is based, at least in part, on an event stored within the memory.

The second previous input may be a reply. Accordingly, each event may comprise: an intent and, where present, at least one slot corresponding to a previous input; a previous output corresponding to the previous input, and where present, a previous reply received in response to the previous output, wherein the output is based, at least in part, on an event stored within the memory.

In some embodiments, the output is based, at least in part, on a plurality of events. Each event may have been generated at any earlier time. Basing the output, at least in part, on an event stored within the memory may be used to further improve user engagement levels. For example, the user may feel well-understood and valued if aspects of their previous input(s) and/or reply(replies), and previous output(s) are considering during the output. Furthermore, the output can be determined in light of the user's holistic experience rather that dealing with a given input in isolation. This more accurately replicates psychotherapy that a user would receive from a human care provider.

The event may further comprise a user engagement level. Consequently, the output may be based, at least on part, on the user engagement level following an event stored within the memory. The event may be associated with a second user. The second user may be any previous user of the method. The system may learn from a plurality of users over time in order to increase the likelihood of maintaining or improving a user's state of wellbeing.

The output may be optimised based on a combination of the input, stored events, predetermined rules and/or statistical methods. Alternatively, or in addition, the output may be based, at least in part, on at least one of: the next stage in a psychotherapy treatment model for the user; the need to obtain a piece of information from the user; and the piece of information required next from the user. Basing the output, at least in part, on at least one of the aforementioned criteria ensures that the output provides a suitable step towards treating a user with respect to a mental health condition. The piece of information required next from the user may be a second input or reply.

The output may be configured to reflect the character of a second user. Configuring the output to reflect the character of a second user, such as a human therapist, may results in a more natural-sounding output in additional to providing familiarity to the user, thus improving the user engagement level. More specifically, the output may be configured to reflect the personality of a human therapist that has previously engaged with the user.

Alternatively, in some embodiments, the output may be configured to differ from the character and/or personality of a second user that has previously engaged with the user. In some scenarios, this may improve a user's engagement level. The output may be personalised for the user.

Furthermore, in some embodiments, the output may be determined, at least in part, based on: a question contained within the input; the frequency of questions contained within the input; the frequency of questions generated by the natural language generation module; the amount of repetition within an input compared to a previous input or reply; or the amount of repetition within an output compared to a previous output. Determining the output, based at least in part, on one of the aforementioned criteria may be used to maintain a predetermined level of user engagement.

In some embodiments, the output may be configured to improve the user's Patient Activation Measure (PAM) score. Alternatively, or in addition, the second output may be configured to improve the user's Patient Activation Measure (PAM) score. The Patient Activation Measure (PAM) may be used to assess the user's knowledge, skill, and confidence for managing their health and/or healthcare.

In some embodiments, the output may be configured to maintain or improve a user's physical and psychological wellbeing.

In some embodiments, the method may comprise sending a multi-component assessment to the user. The multi-component assessment may be configured to determine at least one psychological and/or physical symptom being experienced by a user. These symptoms may inform an individualised treatment plan. This allows the targeted application of behavioural change processes that best meet the user's identified needs. This may include specific psycho-educational activities designed to address the user's psychological and physical difficulties. Thus, in some embodiments, the input may be generated by the user in response to a multi-component assessment.

The input, output and reply may form a part of a conversation. A conversation may comprise a plurality of inputs and/or replies. Alternatively, or in addition, a conversation may comprise a plurality of outputs. A conversation may also comprise an event. More specifically, a conversation may comprise a plurality of events. A conversation may increase the user engagement level and enables a user's state of wellbeing to be improved and/or maintained over a plurality of outputs.

The input, output and/or reply may be asynchronous. Asynchronous inputs, outputs and/or replies enable the user to generate an input or reply at any given time. This may enable the user to engage with or respond to a previous output at a time that best suits them. Alternatively, the input, output and/or reply may be synchronous. A conversation may comprise synchronous and asynchronous inputs, outputs and/or replies. For example, the conversation may comprise a plurality of segments. Each segment may comprise at least one input and at least out output. Each segment may also comprise a reply. Alternatively, or in addition, the reply may be the input in a subsequent segment.

The inputs and outputs within a first segment may be synchronous. Consequently, the first segment may be synchronous. The inputs and outputs within a second segment may be asynchronous. Consequently, the second segment may be asynchronous. The conversation may take place over an extended period of time, such as minutes, hours, day, weeks, months or even years. The conversation may be formed of a sequence of synchronous and asynchronous segments.

The input may be a written, audio and/or visual input. The reply may be a written, audio and/or visual reply. A written, audio and/or visual input and/or reply enables the user to communicate by whichever method is most suitable to them at that time, thus increasing user engagement. Having different input types also enables the user to engage differently at different times depending on what medium is most appropriate under each circumstance. For example, using audio or visual input may not be appropriate when they could disturb others, such as, in the middle of the night, when a written input might be more appropriate.

Alternatively, or in addition, the output may be a written, audio and/or visual output. Similarly, a written, audio and/or visual output enables the user to receive a communication by whichever method is most suitable or most favour by them, thus increasing user engagement. For example, the input, output and/or reply may comprise at least one utterance, sentence, video clip, image, and/or audio snippet. An audio input, output and/or reply may be live speech or a voice recording. Alternatively, or in addition, an audio input, output and/or reply may comprise other sounds or noises, such as laughing, crying and/or screaming. A visual input, output and/or reply may comprise sign language.

The output may comprise a game or task. An output comprising a game or task may increase user engagement.

The method may comprise receiving a plurality of inputs. Each input may result in a corresponding output. Each output may result in a corresponding reply. Alternatively, a plurality of inputs may result in a single output. The inputs, outputs and/or replies may form a conversation. This may increase user engagement and the likelihood of maintaining or improving a user's state of wellbeing.

Alternatively, or in addition, a plurality of inputs enables the user to break down a dialogue into a plurality of discrete inputs, thus enabling the user to communicate in a more natural way. Furthermore, the user may decide to correct, amend or add to a first input by sending a second input.

The inputs may be received over an extended period of time, such as minutes, hours, days, weeks or even months. Receiving the inputs over an extended period of time enables the user to engage at a time that suits them. Accordingly, a plurality of outputs may be determined and/or generated over an extended period of time.

In some embodiments, the plurality of inputs may correspond to different users. For example, a first input may correspond to a first user and a second input may correspond to a second user. For example, the first and second user may be in a support group and/or a coaching group. Alternatively, or in addition, the first and second user may be undergoing treatment and/or therapy within a group. Each input may result in a corresponding output.

The input and/or reply may be sent via a digital delivery channel, such as a mobile phone app, smart speaker and/or website. Alternatively, or in addition, the output may be received by the user via a digital delivery channel, such as a mobile phone app, smart speaker and/or website. Sending inputs and/or replies, and/or receiving outputs via a digital delivery channel enables the user to engage with the computer-implemented method at any given time in any given location. This, in turn, may increase user engagement. Furthermore, the user may vary the digital delivery channel during a predefined treatment model, thus further increasing potential user engagement.

The input, output and/or reply may form part of a predetermined treatment model. The treatment model may be for the treatment of a physical and/or psychological condition. An input, output and/or reply that is part of a predetermined treatment model ensures that users are receiving the most appropriate treatment for their symptoms. This increases the likelihood of the user continuing to engage and increases the likelihood of users improving their state of wellbeing.

The method may further comprise alerting a second user in response to: determining when the input and/or reply is outside of a predetermined treatment model; or determining when the natural language understanding module is unable to determine the intent or, where present, slot associated with the input.

Alerting a second user in response to determining when the input and/or reply is outside of the predetermined treatment model and/or determining when the natural language understanding module is failing to correctly understand the user enables the second user to prevent the user from becoming disengaged and/or receiving inappropriate or inefficient treatment. This improves the user experience and increases the likelihood of improving a user's state of wellbeing.

Alternatively, or in addition, according to the present invention, there is also provided a computer-based system for maintaining or improving a user's state of wellbeing, the system comprising: a conversational agent, which may be divided into a plurality of sub-dialogue units, one of which may be an orchestrator, wherein each of the sub-dialogue units comprises a natural language understanding module configured to receive an input and/or reply and determine at least one intent and, where present, at least one slot within the input and/or reply; a dialogue planning module configured to determine an output based, at least in part, on the at least one intent and/or slot associated within the input and/or reply, and a natural language generation module configured to provide the output to the user.

The system may further comprise a treatment model module which may be part of the orchestrator. The treatment model module may be configured to provide a computer-readable representation of a treatment protocol. More specifically, the treatment model module may be configured to provide a treatment protocol to the orchestrator or the dialogue planning module.

The treatment protocol may be determined based, at least in part, on the input. The treatment protocol may be determined dynamically. Moreover, the treatment protocol may be personalised to the user. For example, the treatment protocol may be personalised based on the obtained user data and/or data obtained during clinical assessment.

The treatment protocol may be a series of steps for improving a user's state of wellbeing. The treatment protocol may be tailored for a specific user state, such as depression or anxiety. The treatment protocol may comprise a series of activities that may be provided to the user in the form of an output. Each activity may be provided in a specified order.

For example, a treatment protocol for Generalised Anxiety Disorder (GAD) may comprise socialising to the model, formulation, journaling worries (worry diary), worry classification, worry themes, worry time, progressive muscle group relaxation (PMGR) and/or planning for the future. A treatment protocol for depression may comprise socialising to the model, formulation, activity journaling, behavioural activation, cognitive restructuring, progressive muscle group relaxation (PMGR) and/or planning for the future.

The system may further comprise a user engagement module. The user engagement module may be configured to determine the user's level of engagement. The user engagement module may be configured to provide a user engagement level to the dialogue planning module. The dialogue planning module may determine an output based, at least in part, on one or more of the user input, the user's engagement level, and a treatment protocol.

The system may further comprise a dialogue history module configured to store previous inputs outputs and, where present, replies. In some embodiments, the dialogue history module comprises the memory.

A dialogue history module configured to store previous inputs, outputs and replies enables the system to generate outputs based on the previous inputs, outputs and/or replies. This enables the system to provide a more human-like output. This may increase effectiveness and/or efficiency with which a user's state of wellbeing is improved or maintained. For example, the output may be based, at least in part, on a previous input, output and/or reply stored within the dialogue history module. Moreover, in some embodiments, the dialogue history module may be configured to store at least one event. More specifically, the dialogue history module may be configured to store: an intent and, where present, at least one slot corresponding to a previous input; a previous output corresponding to the previous input, and where present, a second previous input received subsequent to the previous output. The second previous input may be a previous reply.

The system may further comprise a user data module configured to store information about the user. A user data module enables the system to store user data, which may be used, at least in part, to generate an output. This may enable the system to provide the most effective and/or efficient treatment. For example, the output may be based, at least in part, on user data stored within the user data module.

The system may further comprise a content module configured to store predefined data for providing to the user. The predefined data may comprise videos, games and/or documents. The predefined data may be audio and/or visual data. A content module used to store audio and/or visual data enables the natural language generation module to generate a variety of different output forms.

The predefined data may be provided to the user via a content delivery module. The predefined data may be provided to the user in the form of an output. More specifically, the content delivery module may be configured to provide predefined data to the user as an output based, at least in part, on an output generated by the dialogue planning module.

The style of the output may be configured to replicate the characteristics and/or personality of a second user, thus providing users with a more human-like output. For example, the style of the output may replicate the characteristics and/or personality of a human care provider. Alternatively, in some embodiments, the style of the output may be configured to contrast the characteristics and/or personality of a second user. This may increase user engagement. For example, the output may be based, at least in part, on audio and/or visual data stored within the therapy audio and/or visual data module.

The system may be accessible via any electronic device, such as a computer, laptop, tablet, phone, smart watch and/or appliance. Moreover, the system may be available on or within an existing platform, such as a computer or console game, exercise machine or website.

According to the present invention there is provided a computer-implemented method comprising: receiving an input from a user; simultaneously analysing the input using a natural language understanding module of an active sub-dialogue unit and a natural language understanding module of at least one background sub-dialogue unit, wherein each natural language understanding module is configured to identify, if present within the input, at least one intent from a list of predetermined intents associated with the corresponding sub-dialogue unit; identifying each sub-dialogue unit comprising a natural language understanding module that has identified an intent; determining which one of the identified sub-dialogue units meets a predetermined criterion; selecting the sub-dialogue unit that meets the predetermined criterion; determining an output using a sub-dialogue planning module of the selected sub-dialogue unit, wherein the output is based, at least in part, on the at least one identified intent; and providing the output to the user using an output generation module of the selected sub-dialogue unit.

In order to manage risk, a risk assessment sub-dialogue unit is provided which is configured to receive and analyse all inputs from the user even when the risk assessment sub-dialogue unit is not the active sub-dialogue unit or conversational agent within the system.

The provision of a separate risk assessment sub-dialogue unit avoids the requirement to replicate the risk programming into each separate sub-dialogue unit. This creates a more efficient system, but avoids duplication. However, in order for the risk assessment sub-dialogue unit to function effectively, an adjudicator is provided to enable the risk assessment sub-dialogue unit to interrupt a currently active sub-dialogue unit where an intent identifying risk is identified.

The risk assessment sub-dialogue unit can be called a background sub-dialogue unit in the sense that it listens to all inputs from the user even though it is not the active sub-dialogue unit. Other sub-dialogue units may also be provided that act as background sub-dialogue units. These may include, for example, frequently asked questions or even advertising.

The computer implemented method may be suitable for at least one of managing a digital conversation; managing risk; optimising a conversational agent; and/or providing psychotherapy.

The active sub-dialogue unit may have provided a previous output in response to a previous input.

If a natural language understanding module does not identify an intent from the list of predetermined intents associated with each sub-dialogue unit within the input, it may determine that no intent has been found.

The adjudicator may be used to select the sub-dialogue unit that meets the predetermined criterion.

The output generation module may be a natural language generation module. Alternatively, or in addition, the output generation module may be a multi-media output generation module.

The step of determining which one of the identified sub-dialogue units meets the predetermined criterion consists of one of: determining which one of the identified sub-dialogue units is the active sub-dialogue unit; assigning a predetermined priority value to each sub-dialogue unit and determining the identified sub-dialogue unit having the highest priority value; and determining a confidence value for each sub-dialogue unit, wherein the confidence value indicates how confident the corresponding natural language understanding module is in its identification of the intent, and determining the identified sub-dialogue unit having the highest confidence value.

For example, if the active sub-dialogue unit identifies an intent, it may be selected to determine the output. All of the background sub-dialogue units that identify an intent may be ignored. However, if the active sub-dialogue unit does not identify an intent, the background sub-dialogue units may be consulted, and if any one of them has identified an intent, it may be selected to determine the output. This approach ensures more natural-flowing conversations, with fewer interruptions. As such, background sub-dialogue units may only be used to fill-in the gaps in the understanding capabilities of the active sub-dialogue unit.

In some embodiments, each sub-dialogue unit may be assigned a priority value. If multiple sub-dialogue units identify an intent, the one with the highest priority may be selected to determine the output. The multiple sub-dialogue units may comprise the active and/or background sub-dialogue units. This allows for flexibility in the design of the system, where certain sub-dialogue units get priority over the active sub-dialogue unit, while others do not.

Alternatively, in some embodiments, the natural language understanding modules of each sub-dialogue unit that identifies an intent may produce a confidence value associated with their prediction of a user intent. The confidence value may be implemented using statistical techniques. In such a setting, the sub-dialogue unit that is most confident in its interpretation of the user input may be selected to determine the output.

Alternatively, the step of determining which one of the identified sub-dialogue units meets the predetermined criterion may comprise: calculating an overall score for each identified sub-dialogue unit, wherein the overall score is calculated based on at least one of: determining which one of the identified sub-dialogue units is the active sub-dialogue unit; assigning a predetermined priority value to each sub-dialogue unit; and determining a confidence value for each sub-dialogue unit, wherein the confidence value indicates how confident the corresponding natural language understanding module is in its identification of the intent; and selecting the sub-dialogue unit having the highest overall score.

For example, if multiple sub-dialogue units identify an intent, one with the highest overall priority value may be selected to determine the output. However, if there are multiple sub-dialogue units with the same level of priority, then the one of those with the highest confidence value may be selected to determine the output. Similarly, the priority value assigned to each sub-dialogue unit may be used to select between two or more sub-dialogue units having the same confidence value.

Alternatively, or in addition, if a sub-dialogue unit has determined a previous output, it may not be eligible for determining another output during a given period of time. This can be used to limit the interventions from an advertising sub-dialogue unit, for example. In a clinical context, the priority value assigned to different sub-dialogue units may dynamically change depending on the symptoms, test results and/or stage reached in a user's treatment.

The priority values assigned to each sub-dialogue unit may be automatically determined and/or optimised by learning from user interactions with the system. This may be done by using explicit or implicit indicators of conversation success as an input to data-driven optimisation processes. Additionally, previously recorded conversations can be manually annotated for indicators of success. Situations where the selection of a particular sub-dialogue unit would have been beneficial can also be manually annotated by domain experts.

In some embodiments, there may be multiple previously active sub-dialogue units that have been 'interrupted' in favour of a selected background sub-dialogue unit. This may result in stacked interruptions. For example, a first active sub-dialogue unit may be 'interrupted' if a background sub-dialogue unit is selected to determine the output. The selected background sub-dialogue unit then becomes the second active sub-dialogue unit. This may lead to situations where the first active sub-dialogue unit has lost control in favour of a background sub-dialogue unit, which becomes the second active sub-dialogue unit, and, while the user interacts with the second active sub-dialogue unit, one of their inputs results in subsequent background sub-dialogue unit being selected to determine an output. The subsequent background sub-dialogue unit may then become the third active sub-dialogue unit. Therefore, the adjudicator is configured to keep track of the full conversation stack, noting all previous input, outputs, and/or replies within all previously active sub-dialogue units.

Once the conversation managed by an active sub-dialogue unit ends, the next user input needs to be analysed appropriately. Thus, if stacked interruptions are permitted, a decision needs to be taken on whether the next input goes back to the sub-dialogue unit at the top of the stack i.e. the one most recently interrupted, or to the originally active sub-dialogue unit thus closing all interrupted sub-dialogues simultaneously, or to an orchestrator. Therefore, calculating an overall score for each identified sub-dialogue unit may include deciding which sub-dialogue units were previously active and in which order.

At least one of the sub-dialogue units may be a risk sub-dialogue unit comprising a natural language understanding module configured to identify any intent indicating a risk.

Therefore, the list of predetermined intents associated with the risk natural language understanding module may each indicate a risk. The active sub-dialogue unit may be a risk sub-dialogue unit. Alternatively, at least one of the background sub-dialogue units may be a risk sub-dialogue unit.

The computer-implemented method may further comprise: assigning a predetermined priority value to each sub-dialogue unit, wherein the risk sub-dialogue unit is assigned the highest priority value; receiving an input from a user, wherein the input comprises an intent indicating a risk; identifying each sub-dialogue unit having a natural language understanding module that has identified an intent; determining that the risk sub-dialogue unit is the identified sub-dialogue unit having the highest priority value; selecting the risk sub-dialogue unit; determining an output using a sub-dialogue planning module of the risk sub-dialogue unit, wherein the output is based, at least in part, on the intent indicating a risk; and providing the output to the user using an output generation module of the risk sub-dialogue unit.

The output may be configured to confirm the presence of the intent indicating a risk within the input. Alternatively, or in addition, the output may seek to confirm the presence of the intent indicating a risk within the input. For example, the output may comprise a question relating to the presence of the intent indicating a risk.

The method may further comprise: receiving, in response to the output, a reply from the user confirming the presence of the intent indicating a risk.

The reply may be received by the natural language understanding module of the risk sub-dialogue unit. The risk natural language understanding module may be configured to identify, if present within the reply, at least one intent from a subsequent list of predetermined intents associated with the corresponding sub-dialogue unit. The subsequent list of predetermined intents may be a different list to the original list of predetermined intents associated with the corresponding sub-dialogue unit. Alternatively, it may be the same list.

In response to identifying at least one intent from the subsequent list of predetermined intents, the corresponding dialogue planning module may determine at least one subsequent output. The at least one subsequent output may be provided to the user using an output generation module.

Alternatively, the reply from the user may deny the presence of the intent indicating a risk. In this case, the reply may be treated as an input and the method restarted. Alternatively, an alternative intent within the original input may be analysed and responded to instead.

The method may further comprise: providing, using the output generation module of the risk sub-dialogue unit, at least one subsequent output to the user, wherein at least one subsequent output is configured to determine the severity of the risk associated with the intent indicating a risk.

The at least one subsequent output may be based, at least in part, on the input and/or reply. For example, the subsequent output may comprise at least one questions relating to the intent indicating a risk.

The method may further comprise: receiving at least one subsequent reply from the user; and estimating the severity of the risk based, at least in part, on the input, reply and/or at least one subsequent reply.

The severity of the risk may be estimated by identifying the category of risk into which the intent falls. Each category of risk has a different response appropriate to the risk expressed.

The method may further comprise taking an action, wherein the action is based, at least on part, on the estimated severity of the risk. For example, if the severity of the risk is low, the additional action may comprise logging the intent indicating a risk within a memory or sending a notification to the user's clinician. In addition, the output may comprise providing advice to the user. Conversely, if the severity of the risk is high, the action may comprise alerting emergency services. The user would also receive an appropriate output.

Each natural language understanding module may be further configured to identify, where present, at least one slot within the input; and wherein the corresponding output, if determined, is based, at least in part, on the at least one identified slot.

Determining the output based, at least in part, on the intent and/or slot associated with the input enables the exchange between the computer system and the user to be more conversational, thus improving user engagement.

The reply and/or subsequent reply may be the input for a subsequent iteration of the method. In other words, the input may be a previous reply.

Furthermore, according to the present invention there is provided a conversational agent comprising: an active sub-dialogue unit comprising: a natural language understanding module configured to receive an input from a user and, if present within the input, identify an intent from a list of predetermined intents associated with the active sub-dialogue unit; a sub-dialogue planning module configured to determine an output based, at least in part, on the identified intent from the list of predetermined intents associated with the active sub-dialogue unit; and an output generation module configured to provide the output, if determined, to the user; at least one background sub-dialogue unit comprising: a natural language understanding module configured to receive the input from the user and, if present within the input, identify an intent from a list of predetermined intents associated with the background sub-dialogue unit; a sub-dialogue planning module configured to determine an output based, at least in part, on the identified intent from the list of predetermined intents associated with the background sub-dialogue unit; and an output generation module configured to provide the output, if determined, to the user; and an adjudicator configured to: identify each sub-dialogue unit comprising a natural language understanding module that identifies an intent; determine which one of the identified sub-dialogue units meets a predetermined criterion; and select the sub-dialogue unit that meets the predetermined criterion such that only the selected sub-dialogue unit determines and provides an output to the user in response to each input.

In some embodiments, the input may be a reply, from the user, in response to a previous output.

According to the present invention there is provided a computer-implemented method comprising: receiving an input from a user; simultaneously analysing the input using a natural language understanding module of an active sub-dialogue unit and a natural language understanding module of at least one background sub-dialogue unit, wherein each natural language understanding module is configured to identify, if present within the input, at least one intent from a list of predetermined intents associated with the corresponding sub-dialogue unit; identifying each sub-dialogue unit comprising a natural language understanding module that has identified an intent; determining which one of the identified sub-dialogue units meets a predetermined criterion; selecting the sub-dialogue unit that meets the predetermined criterion; determining an output using a sub-dialogue planning module of the selected sub-dialogue unit, wherein the output is based, at least in part, on the at least one identified intent; and providing the output to the user using an output generation module of the selected sub-dialogue unit.

In order to manage risk, a risk assessment sub-dialogue unit is provided which is configured to receive and analyse all inputs from the user even when the risk assessment sub-dialogue unit is not the active sub-dialogue unit or conversational agent within the system.

The provision of a separate risk assessment sub-dialogue unit avoids the requirement to replicate the risk programming into each separate sub-dialogue unit. This creates a more efficient system, but avoids duplication. However, in order for the risk assessment sub-dialogue unit to function effectively, an adjudicator is provided to enable the risk assessment sub-dialogue unit to interrupt a currently active sub-dialogue unit where an intent identifying risk is identified.

The risk assessment sub-dialogue unit can be called a background sub-dialogue unit in the sense that it listens to all inputs from the user even though it is not the active sub-dialogue unit. Other sub-dialogue units may also be provided that act as background sub-dialogue units. These may include, for example, frequently asked questions or even advertising.

The computer implemented method may be suitable for at least one of managing a digital conversation; managing risk; optimising a conversational agent; and/or providing psychotherapy.

The active sub-dialogue unit may have provided a previous output in response to a previous input.

If a natural language understanding module does not identify an intent from the list of predetermined intents associated with each sub-dialogue unit within the input, it may determine that no intent has been found.

The adjudicator may be used to select the sub-dialogue unit that meets the predetermined criterion.

The output generation module may be a natural language generation module. Alternatively, or in addition, the output generation module may be a multi-media output generation module.

The step of determining which one of the identified sub-dialogue units meets the predetermined criterion consists of one of: determining which one of the identified sub-dialogue units is the active sub-dialogue unit; assigning a predetermined priority value to each sub-dialogue unit and determining the identified sub-dialogue unit having the highest priority value; and determining a confidence value for each sub-dialogue unit, wherein the confidence value indicates how confident the corresponding natural language understanding module is in its identification of the intent, and determining the identified sub-dialogue unit having the highest confidence value.

For example, if the active sub-dialogue unit identifies an intent, it may be selected to determine the output. All of the background sub-dialogue units that identify an intent may be ignored. However, if the active sub-dialogue unit does not identify an intent, the background sub-dialogue units may be consulted, and if any one of them has identified an intent, it may be selected to determine the output. This approach ensures more natural-flowing conversations, with fewer interruptions. As such, background sub-dialogue units may only be used to fill-in the gaps in the understanding capabilities of the active sub-dialogue unit.

In some embodiments, each sub-dialogue unit may be assigned a priority value. If multiple sub-dialogue units identify an intent, the one with the highest priority may be selected to determine the output. The multiple sub-dialogue units may comprise the active and/or background sub-dialogue units. This allows for flexibility in the design of the system, where certain sub-dialogue units get priority over the active sub-dialogue unit, while others do not.

Alternatively, in some embodiments, the natural language understanding modules of each sub-dialogue unit that identifies an intent may produce a confidence value associated with their prediction of a user intent. The confidence value may be implemented using statistical techniques. In such a setting, the sub-dialogue unit that is most confident in its interpretation of the user input may be selected to determine the output.

Alternatively, the step of determining which one of the identified sub-dialogue units meets the predetermined criterion may comprise: calculating an overall score for each identified sub-dialogue unit, wherein the overall score is calculated based on at least one of: determining which one of the identified sub-dialogue units is the active sub-dialogue unit; assigning a predetermined priority value to each sub-dialogue unit; and determining a confidence value for each sub-dialogue unit, wherein the confidence value indicates how confident the corresponding natural language understanding module is in its identification of the intent; and selecting the sub-dialogue unit having the highest overall score.

For example, if multiple sub-dialogue units identify an intent, one with the highest overall priority value may be selected to determine the output. However, if there are multiple sub-dialogue units with the same level of priority, then the one of those with the highest confidence value may be selected to determine the output. Similarly, the priority value assigned to each sub-dialogue unit may be used to select between two or more sub-dialogue units having the same confidence value.

Alternatively, or in addition, if a sub-dialogue unit has determined a previous output, it may not be eligible for determining another output during a given period of time. This can be used to limit the interventions from an advertising sub-dialogue unit, for example. In a clinical context, the priority value assigned to different sub-dialogue units may dynamically change depending on the symptoms, test results and/or stage reached in a user's treatment.

The priority values assigned to each sub-dialogue unit may be automatically determined and/or optimised by learning from user interactions with the system. This may be done by using explicit or implicit indicators of conversation success as an input to data-driven optimisation processes. Additionally, previously recorded conversations can be manually annotated for indicators of success. Situations where the selection of a particular sub-dialogue unit would have been beneficial can also be manually annotated by domain experts.

In some embodiments, there may be multiple previously active sub-dialogue units that have been 'interrupted' in favour of a selected background sub-dialogue unit. This may result in stacked interruptions. For example, a first active sub-dialogue unit may be 'interrupted' if a background sub-dialogue unit is selected to determine the output. The selected background sub-dialogue unit then becomes the second active sub-dialogue unit. This may lead to situations where the first active sub-dialogue unit has lost control in favour of a background sub-dialogue unit, which becomes the second active sub-dialogue unit, and, while the user interacts with the second active sub-dialogue unit, one of their inputs results in subsequent background sub-dialogue unit being selected to determine an output. The subsequent background sub-dialogue unit may then become the third active sub-dialogue unit. Therefore, the adjudicator is configured to keep track of the full conversation stack, noting all previous input, outputs, and/or replies within all previously active sub-dialogue units.

Once the conversation managed by an active sub-dialogue unit ends, the next user input needs to be analysed appropriately. Thus, if stacked interruptions are permitted, a decision needs to be taken on whether the next input goes back to the sub-dialogue unit at the top of the stack i.e. the one most recently interrupted, or to the originally active sub-dialogue unit thus closing all interrupted sub-dialogues simultaneously, or to an orchestrator. Therefore, calculating an overall score for each identified sub-dialogue unit may include deciding which sub-dialogue units were previously active and in which order.

At least one of the sub-dialogue units may be a risk sub-dialogue unit comprising a natural language understanding module configured to identify any intent indicating a risk.

Therefore, the list of predetermined intents associated with the risk natural language understanding module may each indicate a risk. The active sub-dialogue unit may be a risk sub-dialogue unit. Alternatively, at least one of the background sub-dialogue units may be a risk sub-dialogue unit.

The computer-implemented method may further comprise: assigning a predetermined priority value to each sub-dialogue unit, wherein the risk sub-dialogue unit is assigned the highest priority value; receiving an input from a user, wherein the input comprises an intent indicating a risk; identifying each sub-dialogue unit having a natural language understanding module that has identified an intent; determining that the risk sub-dialogue unit is the identified sub-dialogue unit having the highest priority value; selecting the risk sub-dialogue unit; determining an output using a sub-dialogue planning module of the risk sub-dialogue unit, wherein the output is based, at least in part, on the intent indicating a risk; and providing the output to the user using an output generation module of the risk sub-dialogue unit.

The output may be configured to confirm the presence of the intent indicating a risk within the input. Alternatively, or in addition, the output may seek to confirm the presence of the intent indicating a risk within the input. For example, the output may comprise a question relating to the presence of the intent indicating a risk.

The method may further comprise: receiving, in response to the output, a reply from the user confirming the presence of the intent indicating a risk.

The reply may be received by the natural language understanding module of the risk sub-dialogue unit. The risk natural language understanding module may be configured to identify, if present within the reply, at least one intent from a subsequent list of predetermined intents associated with the corresponding sub-dialogue unit. The subsequent list of predetermined intents may be a different list to the original list of predetermined intents associated with the corresponding sub-dialogue unit. Alternatively, it may be the same list.

In response to identifying at least one intent from the subsequent list of predetermined intents, the corresponding dialogue planning module may determine at least one subsequent output. The at least one subsequent output may be provided to the user using an output generation module.

Alternatively, the reply from the user may deny the presence of the intent indicating a risk. In this case, the reply may be treated as an input and the method restarted. Alternatively, an alternative intent within the original input may be analysed and responded to instead.

The method may further comprise: providing, using the output generation module of the risk sub-dialogue unit, at least one subsequent output to the user, wherein at least one subsequent output is configured to determine the severity of the risk associated with the intent indicating a risk.

The at least one subsequent output may be based, at least in part, on the input and/or reply. For example, the subsequent output may comprise at least one questions relating to the intent indicating a risk.

The method may further comprise: receiving at least one subsequent reply from the user; and estimating the severity of the risk based, at least in part, on the input, reply and/or at least one subsequent reply.

The severity of the risk may be estimated by identifying the category of risk into which the intent falls. Each category of risk has a different response appropriate to the risk expressed.

The method may further comprise taking an action, wherein the action is based, at least on part, on the estimated severity of the risk. For example, if the severity of the risk is low, the additional action may comprise logging the intent indicating a risk within a memory or sending a notification to the user's clinician. In addition, the output may comprise providing advice to the user. Conversely, if the severity of the risk is high, the action may comprise alerting emergency services. The user would also receive an appropriate output.

Each natural language understanding module may be further configured to identify, where present, at least one slot within the input; and wherein the corresponding output, if determined, is based, at least in part, on the at least one identified slot.

Determining the output based, at least in part, on the intent and/or slot associated with the input enables the exchange between the computer system and the user to be more conversational, thus improving user engagement.

The reply and/or subsequent reply may be the input for a subsequent iteration of the method. In other words, the input may be a previous reply.

Furthermore, according to the present invention there is provided a conversational agent comprising: an active sub-dialogue unit comprising: a natural language understanding module configured to receive an input from a user and, if present within the input, identify an intent from a list of predetermined intents associated with the active sub-dialogue unit; a sub-dialogue planning module configured to determine an output based, at least in part, on the identified intent from the list of predetermined intents associated with the active sub-dialogue unit; and an output generation module configured to provide the output, if determined, to the user; at least one background sub-dialogue unit comprising: a natural language understanding module configured to receive the input from the user and, if present within the input, identify an intent from a list of predetermined intents associated with the background sub-dialogue unit; a sub-dialogue planning module configured to determine an output based, at least in part, on the identified intent from the list of predetermined intents associated with the background sub-dialogue unit; and an output generation module configured to provide the output, if determined, to the user; and an adjudicator configured to: identify each sub-dialogue unit comprising a natural language understanding module that identifies an intent; determine which one of the identified sub-dialogue units meets a predetermined criterion; and select the sub-dialogue unit that meets the predetermined criterion such that only the selected sub-dialogue unit determines and provides an output to the user in response to each input.

In some embodiments, the input may be a reply, from the user, in response to a previous output.

A conversational agent may be required to maintain a conversation with its user that includes tens or even hundreds of inputs and outputs, spread throughout multiple days, or weeks. As the complexity of the designed interaction increases, that may have a detrimental effect on the performance of the system, and on its ease of development. A dialogue unit may be comprised of a natural language understanding (NLU) module, a dialogue planning (DP) module, and an output generation module. The output generation module may be a natural language generating (NLG) module. Dialogues that are more complex require the NLU module to be able to identify a greater number of intents and, where present, slots, which can lead to a drop in accuracy. This may pose a limit in complexity, beyond which the NLU accuracy is simply no longer sufficient for achieving a natural interaction. Longer lasting, and more complex conversations can lead to a DP module that is hard to design, implement, and maintain. This increases the costs of system development, and may again impose a limit on the complexity of the conversation, beyond which implementing a suitable DP module is no longer economically feasible.

One method to limit the complexity of a dialogue in a conversational agent, while increasing the complexity of the interaction model, is to break up a longer conversation into stages. Each stage can then be implemented as its own sub-dialogue, which has a lower complexity than would be required for the overall interaction. Crucially, each sub-dialogue has a significantly lower level of complexity compared to the overall conversation. Each sub-dialogue may be provided by a different sub-dialogue unit.

This approach is particularly well suited for structured conversations, such as would be encountered in the delivery of psychotherapy treatment protocol, or in the delivery of educational content. For example, in a psychotherapy context, the conversation may advance from one topic to another, moving from assessment of the patient symptoms, to understanding their goals in therapy, to psychoeducation, to the presentation of coping techniques, to experiential experiments, and so on. Each of these stages may be implemented as a self-contained and relatively simple sub-dialogue.

The output generation module of the active sub-dialogue unit may be a natural language generation module. Alternatively, the output generation module of the active sub-dialogue unit may be a multi-media generation module.

The output generation module of at least one background sub-dialogue unit may be a natural language generation module. Alternatively, the output generation module of at least one, or each, background sub-dialogue unit may be a multi-media generation module.

The natural language understanding module of at least one sub-dialogue unit may be configured to identify, where present, at least one slot within the input; and wherein the corresponding output, if determined, is based, at least in part, on the at least one identified slot.

As previously disclosed, determining the output based, at least in part, on the intent and/or slot associated with the input enables the exchange between the computer system and the user to be more conversational, thus improving user engagement.

The list of predetermined intents associated with the active sub-dialogue unit may be different from the list of predetermined intents associated with the background sub-dialogue unit.

However, at least one intent may be present on two or more different predetermined lists. As such, different predetermined lists may only comprise one difference. However, in some embodiments, different predetermined lists may comprise multiple differences or may be completely different. Also, in some embodiments the list of predetermined intents associated with the active sub-dialogue unit may be the same as the list of predetermined intents associated with the background sub-dialogue unit.

At least one sub-dialogue unit may be a risk sub-dialogue unit comprising: a natural language understanding module configured to receive the input from the user and, if present within the input, identify an intent indicating a risk; a sub-dialogue planning module configured to determine an output based, at least in part, on the identified intent indicating a risk; and an output generation module configured to provide the output to the user when facilitated by the adjudicator.

For example, in a clinical setting, therapists delivering care have a responsibility to monitor their patient for signs of risk to self or others. A similar responsibility may be assigned to the conversational agent. The watchful monitoring of user inputs for intents indicating a risk may be permanently present throughout a clinical conversation, regardless of the point currently reached in the interaction.

The risk sub-dialogue unit may be triggered by user inputs that include potential intents indicating a risk. Once triggered, the risk sub-dialogue unit may be selected to provide an output to the user.

The risk sub-dialogue unit may be further configured to take an action, and wherein the action is based, at least on part, on the identified risk.

For example, the risk sub-dialogue unit may be configured to confirm the presence of the risk and/or estimate the severity of the risk. The risk sub-dialogue unit may be further configured to enact one or more of a set of actions, depending on the outcomes of the discovery interaction. The actions may range from notifying the user's treating clinician, launching a crisis management procedure, involving clinical personnel, and/or calling out to the local emergency services, as appropriate.

The conversational agent may comprise a plurality of sub-dialogue units, one of which may be an orchestrator and one of which may be a background sub-dialogue unit. At any one time, only one sub-dialogue unit is active, in the sense that it is providing outputs to the user. The background sub-dialogue units are configured to receive each input.

The background sub-dialogue unit may be a risk sub-dialogue unit; a chitchat sub-dialogue unit; a conversation repair sub-dialogue unit; and FAQ sub-dialogue unit; an escalation sub-dialogue unit or an advertising sub-dialogue unit.

At least one of the sub-dialogue units may be a treatment sub-dialogue unit. Each treatment sub-dialogue unit may be use to deliver an element of care. Each element of care may comprise its own internal structure. For example, for "Defusion", a typical element of care may include an introduction, a range of explanations and exercises through which the user can be guided. The element of care may further comprise elements of measurement (delivered as questionnaires or conversations) that can be used to track the progress that the user is making through the programme, and to measure the extent to which the required knowledge and understanding has been absorbed and internalised. A plurality of elements of care may be used to deliver a treatment protocol.

The orchestrator may be responsible for guiding the user from one sub-dialogue unit to another. Once an element of care managed by the active sub-dialogue unit is completed by the user, control may be handed back to the orchestrator. The orchestrator may be responsible for the conversations that the user has with the conversational agent until the next sub-dialogue unit becomes activated.

In addition, the orchestrator may be responsible for presenting the user with a unified experience, which hides the modular construction of the conversational agent. For technical reasons, it is preferable to limit the complexity of any one dialogue, therefore sub-dialogues are used to split the overall conversation into manageable smaller parts. However, it may not be desirable for the user to be presented with a fragmented user experience. Therefore, the orchestrator provides the conversational bridging that gives the illusion of a single long-lasting conversation.

The invention will now be further and more particularly described, by way of example only, with reference to the accompanying drawings.

Figure 1:
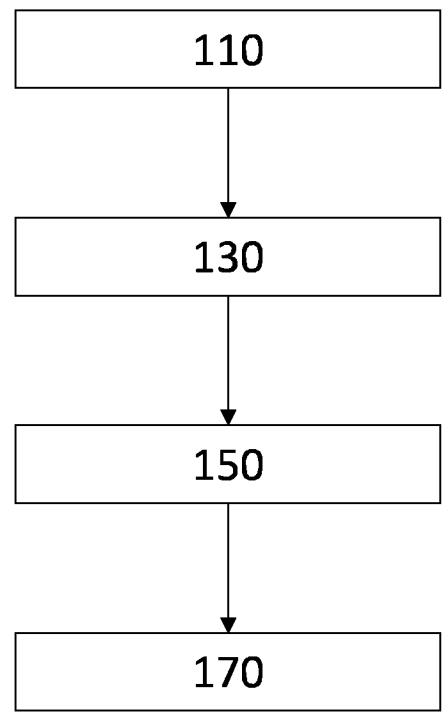
FIG. 1 shows a computer-implemented method for maintaining or improving a user's state of wellbeing according to some embodiments of the invention.

FIG. 1 shows a computer-implemented method for maintaining or improving a user's state of wellbeing according to some embodiments of the invention. The method comprises receiving an input from a user 110; analysing the input using a natural language understanding module 130; determining an output using a dialogue planning module 150; and providing the output to the user using a natural language generation module 170.

More specifically, the natural language understanding module 130 is configured to determine at least one intent and, where present, at least one slot within the input. Moreover, the output is based, at least in part, on the intent and/or slot associated with the input.

In some embodiments, the output is determined, via the dialogue planning module, using a combination of predetermined rules and statistical methods.

Figure 2:
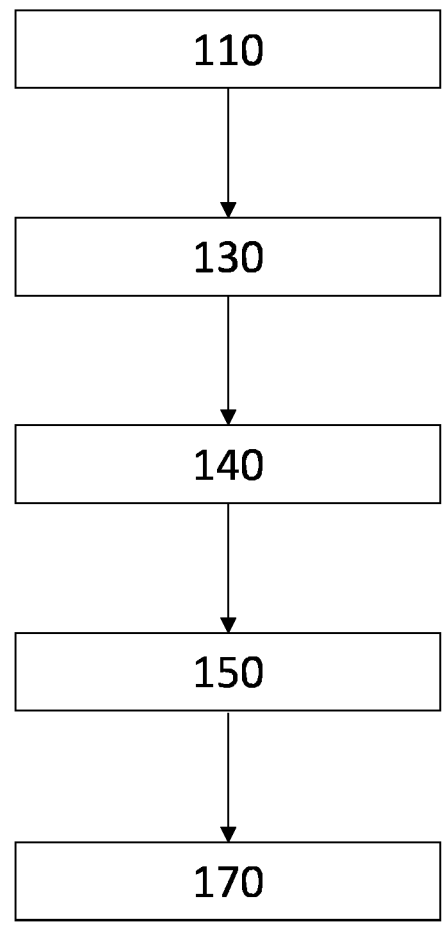
FIG. 2 shows a computer-implemented method for maintaining or improving a user's state of wellbeing according to some embodiments of the invention.

FIG. 2 shows a computer-implemented method for maintaining or improving a user's state of wellbeing according to some embodiments of the invention. The method comprises receiving an input from a user 110; analysing the input using a natural language understanding module 130; determining a user engagement level 140; determining an output using a dialogue planning module 150; and providing the output to the user using a natural language generation module 170.

More specifically, the output is based, at least in part, on the user engagement level. Consequently, the output is based, at least in part, on the at least one intent and/or slot associated with the input and on the user engagement level.

Figure 3:
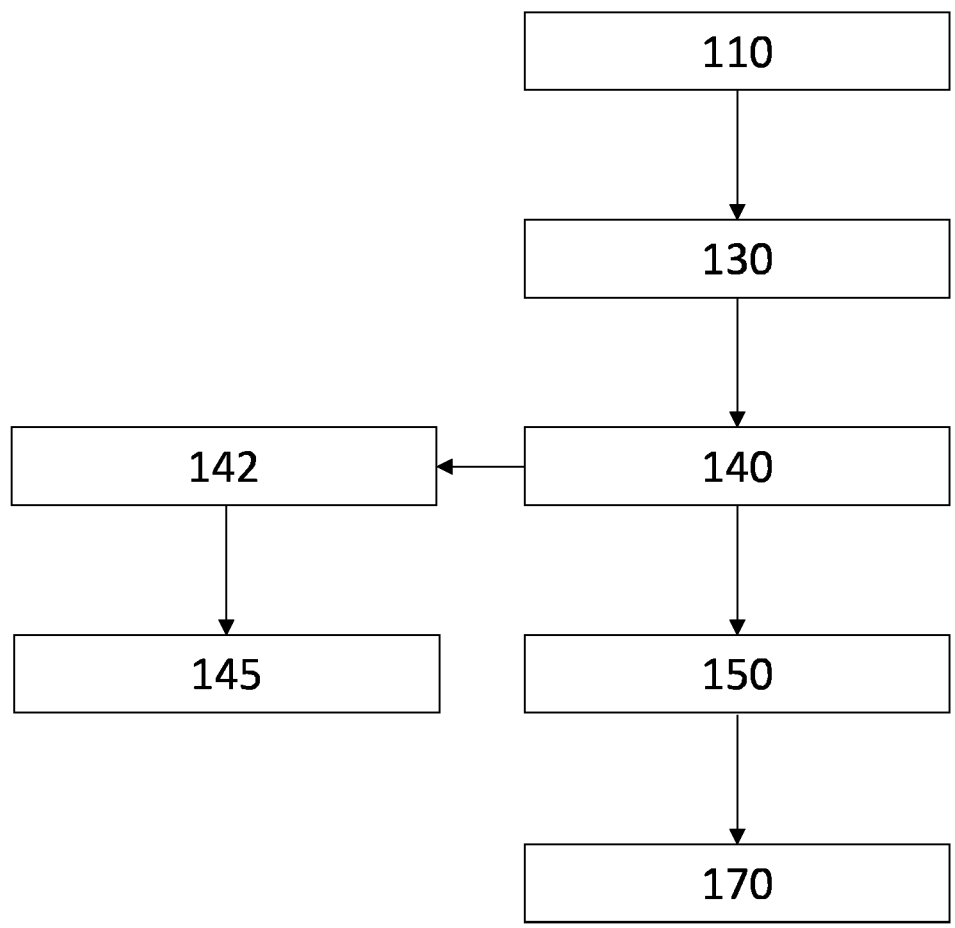
FIG. 3 shows a computer-implemented method for maintaining or improving a user's state of wellbeing according to some embodiments of the invention.

FIG. 3 shows a computer-implemented method for maintaining or improving a user's state of wellbeing according to some embodiments of the invention. The method comprises receiving an input from a user 110; analysing the input using a natural language understanding module 130; determining a user engagement level 140; determining an output using a dialogue planning module 150; and providing the output to the user using a natural language generation module 170, wherein the method further comprises determining if the user engagement level is below a predetermined threshold 142; and sending an alert to a second user 145 upon determining a user engagement level below the predetermined threshold.

Figure 4:
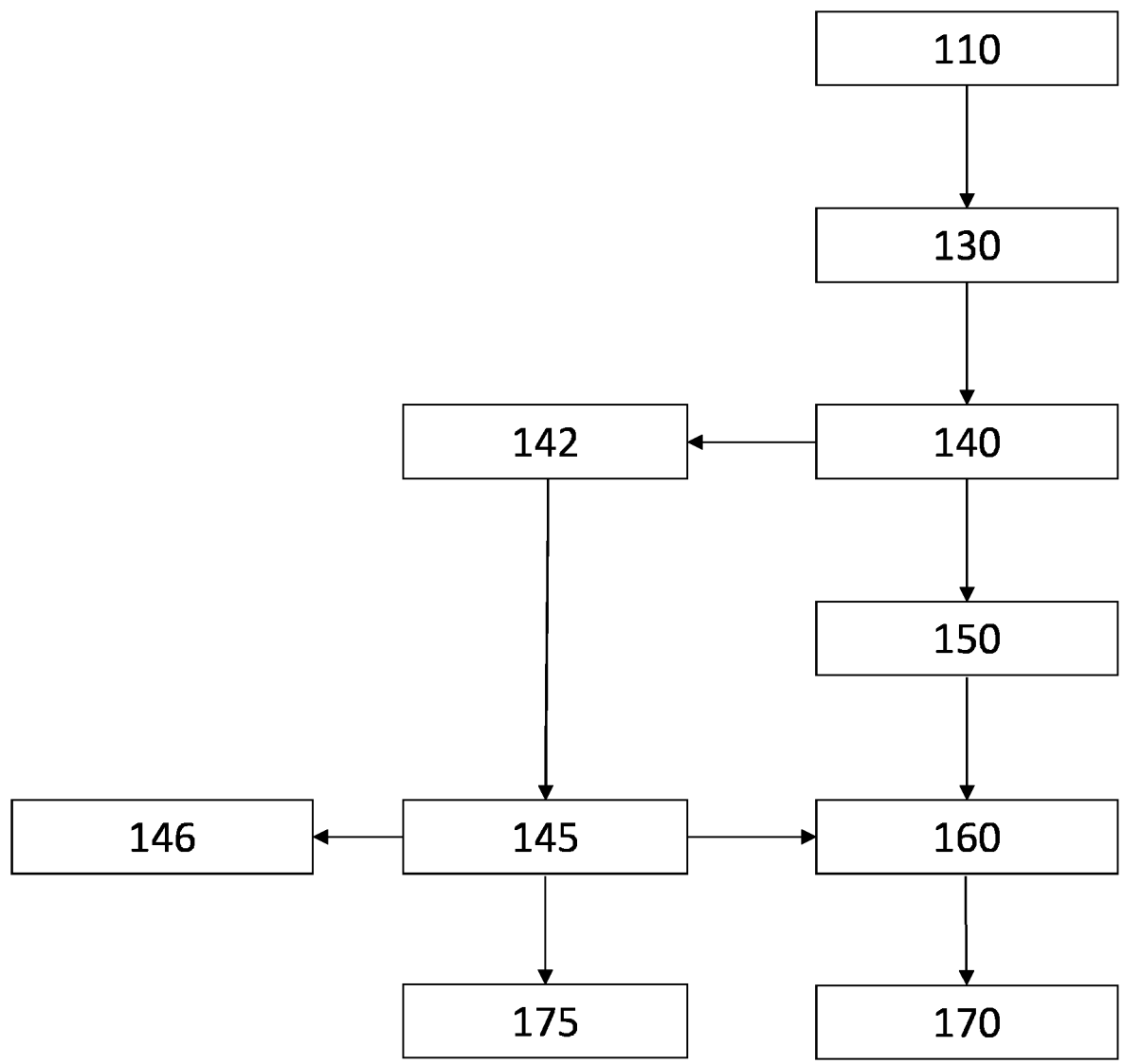
FIG. 4 shows a computer-implemented method for maintaining or improving a user's state of wellbeing according to some embodiments of the invention.

FIG. 4 shows a computer-implemented method for maintaining or improving a user's state of wellbeing according to some embodiments of the invention. As shown in FIG. 4, after having received the alert 145, the second user may provide a second output to the user 175. Alternatively, or in addition, after having received the alert 145, the second user may amend the output determined by the dialogue planning module 160. Conversely, after having received the alert 145, the second user may do nothing 146.

Figure 5:
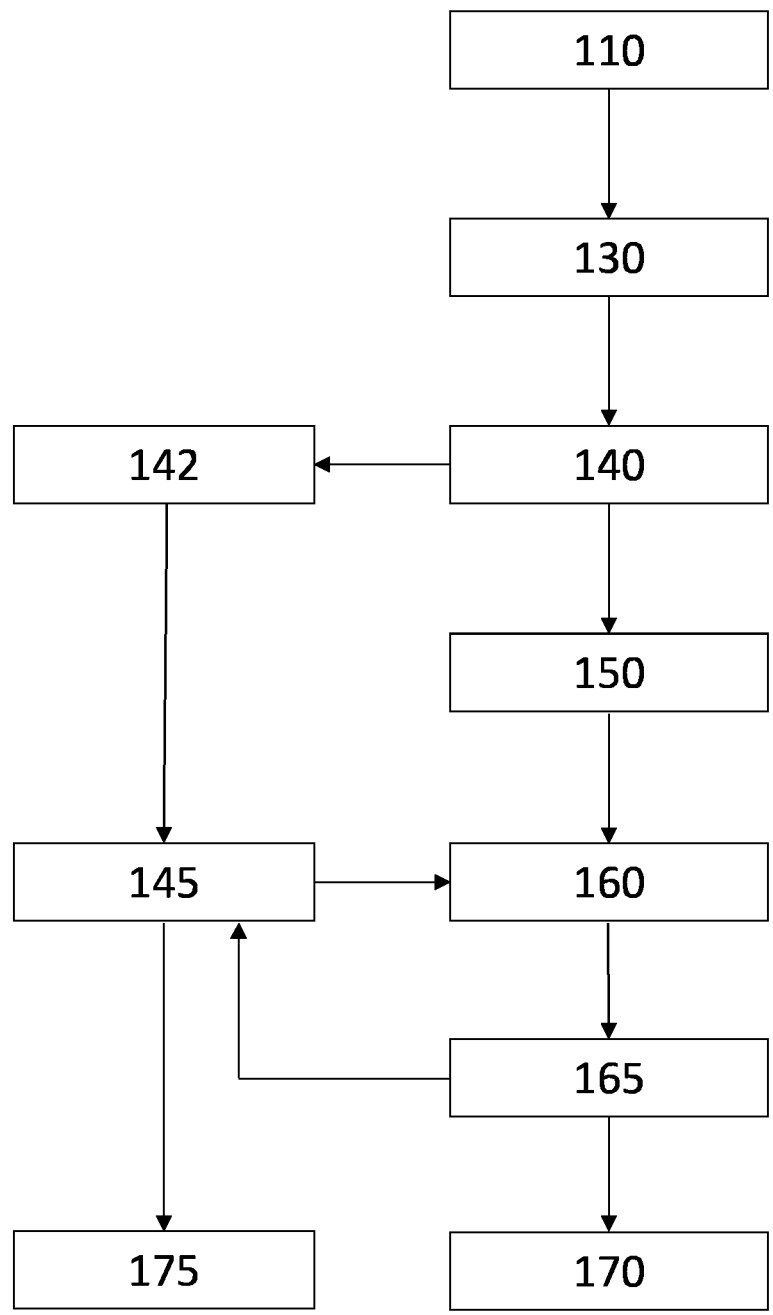
FIG. 5 shows a computer-implemented method for maintaining or improving a user's state of wellbeing according to some embodiments of the invention.

FIG. 5 shows a computer-implemented method for maintaining or improving a user's state of wellbeing according to some embodiments of the invention. As shown in FIG. 5, the method comprises reviewing the amended output 160 and providing further amendments where needed 165. If no further amendments are needed, the amended output 160 is sent to the user 170. Where further amendments are needed, the further amended output 165 is sent to the second user for review. The second user may then make further amendments 160. This review and amendment cycle may repeat any number of times. For example, the second user may amend the output 1, 2, 3, 4, 5, or more than 5 times.

The second user 145 is at least one of a human care provider, family member of the first user or friend of the first user.

Alternatively, in some embodiments, the method comprises reviewing the amended output and providing further amendments where needed 165. The further amended output is then sent directly to the user 170.

Figure 6:
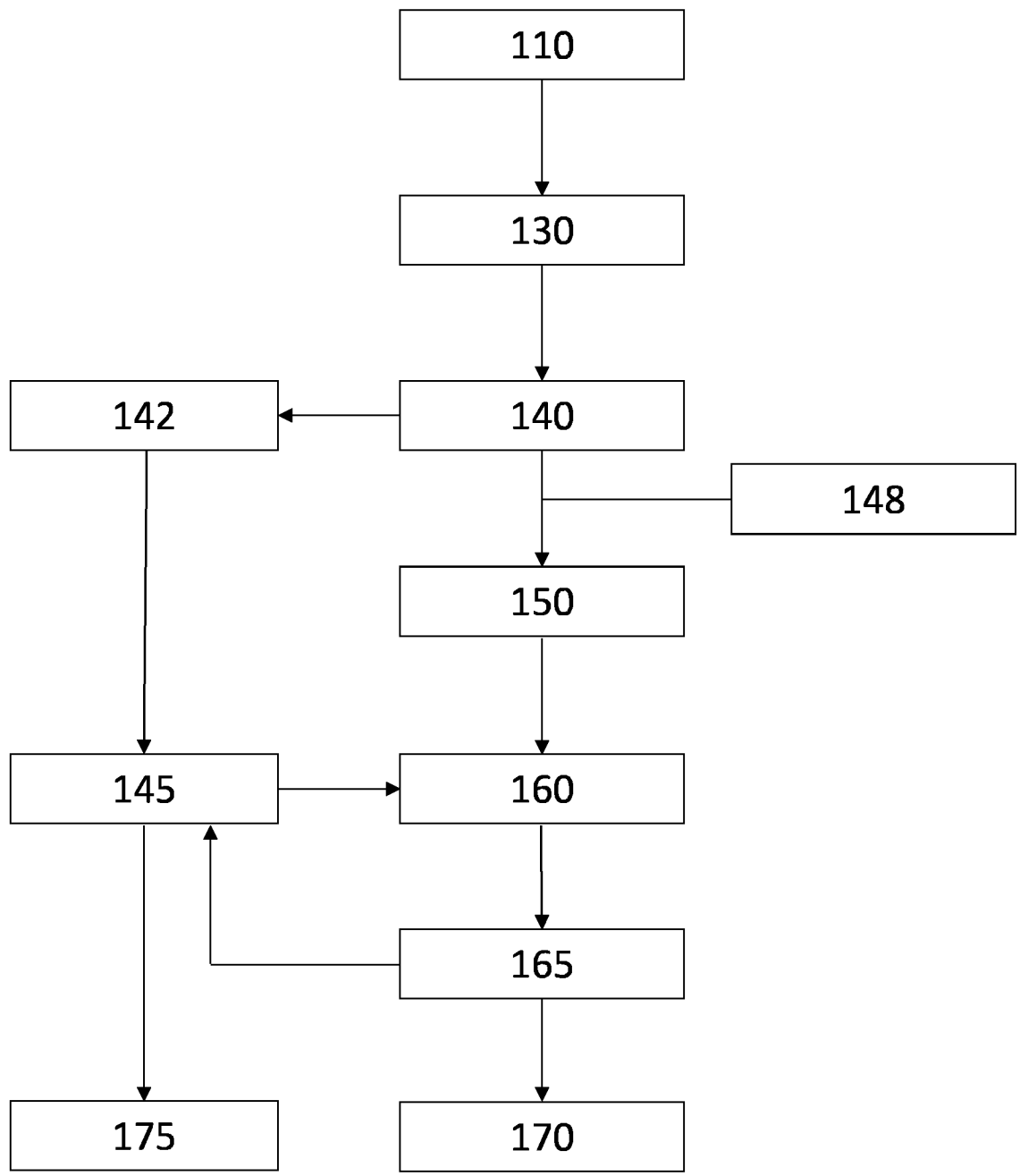
FIG. 6 shows a computer-implemented method for maintaining or improving a user's state of wellbeing according to some embodiments of the invention.

FIG. 6 shows a computer-implemented method for maintaining or improving a user's state of wellbeing according to some embodiments of the invention. The method comprises reviewing a memory 148 configured to store at least one event. Each event comprises an intent and, where present, at least one slot corresponding to a previous input; a previous output corresponding to the previous input; and where present, a second previous input received subsequent to the previous output. Consequently, the output is based, at least in part, on an event stored within the memory. More specifically, the output is optimized based on a combination of the input, stored events, predetermined rules and/or statistical methods.

Alternatively, or in addition, the output is based, at least in part, on at least one of the next stage in a psychotherapy treatment model for the user; the need to obtain a piece of information from the user; and the piece of information required next from the user.

Alternatively, or in addition, the output is determined, at least in part, based on a question contained within the input; the frequency of questions contained within the input; the frequency of questions generated by the natural language generation module; the amount of repetition within an input compared to a previous input; and/or the amount of repetition within an output compared to a previous output. In some embodiments, the output is configured to reflect the character of a second user. Alternatively, or in addition, at least one of the input and output form part of a predetermined treatment model.

In some embodiments, the method further comprises: determining whether the input is within a predetermined treatment model; and alerting a second user upon determining an input that is not within the predetermined treatment model.

Alternatively, or in addition, the method may further comprise: determining when the natural language understanding module is unable to determine the intent or, where present, slot associated with the input; and alerting a second user upon determining that the natural language understanding module is unable to determine the intent or, where present, slot associated with the input.

Each of FIGS. 1 to 6 shows a computer-implemented method for maintaining or improving a user's state of wellbeing. This method may be carried out using a conversational agent and/or one or more sub-dialogue units.

Figure 7:
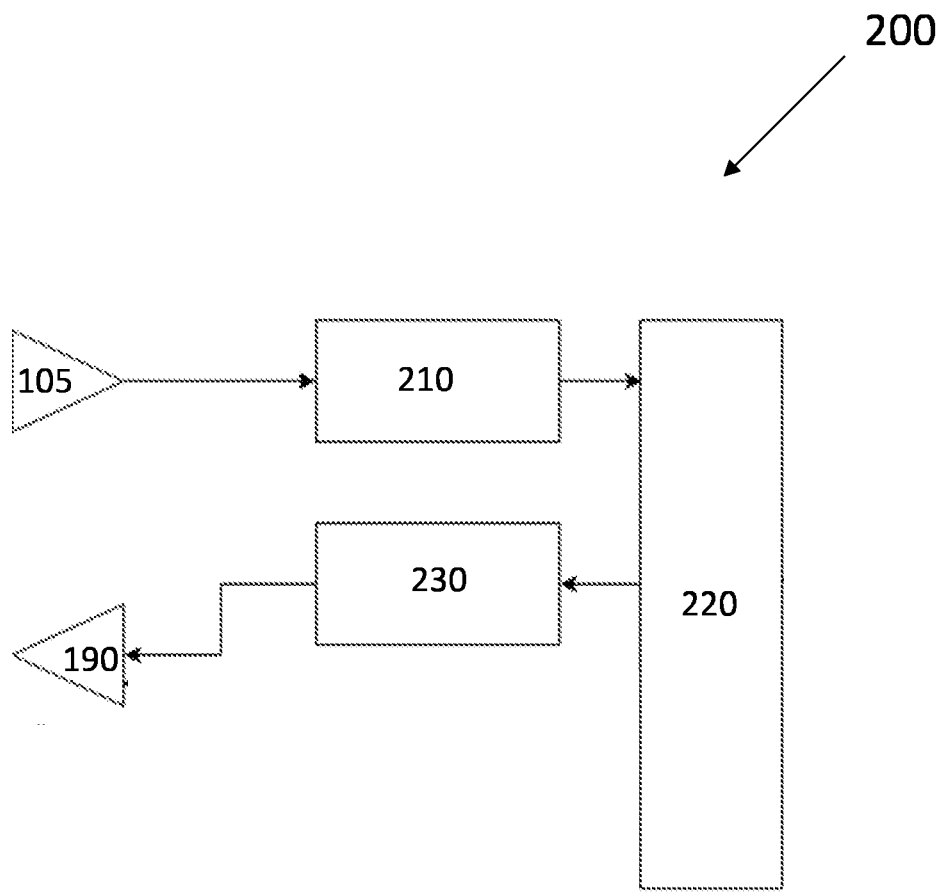
FIG. 7 shows a computer-based system for maintaining or improving a user's state of wellbeing.

FIG. 7 shows a computer-based system for maintaining or improving a user's state of wellbeing. The system 200 comprises a natural language understanding module 210, a dialogue planning module 220 and a natural language generation module 230. The natural language understanding module 210, a dialogue planning module 220 and a natural language generation module 230 form part of a conversational agent. More specifically, the natural language understanding module 210, dialogue planning module 220 and natural language generation module 230 form a sub-dialogue unit. A plurality of sub-dialogue units forms a conversational agent.

The natural language understanding module 210 is configured to receive an input 105 and determine at least one intent and, where present, at least one slot within the input. The dialogue planning module 220 is configured to determine an output 190 based, at least in part, on the intent and/or slot associated within the input. The natural language generation module 230 is configured to provide the output 190 to the user.

More specifically, the natural language understanding module 210 is configured to identify, if present within the input and/or reply, at least one intent from a list of predetermined intents associated with the sub-dialogue unit 200.

Figure 8:
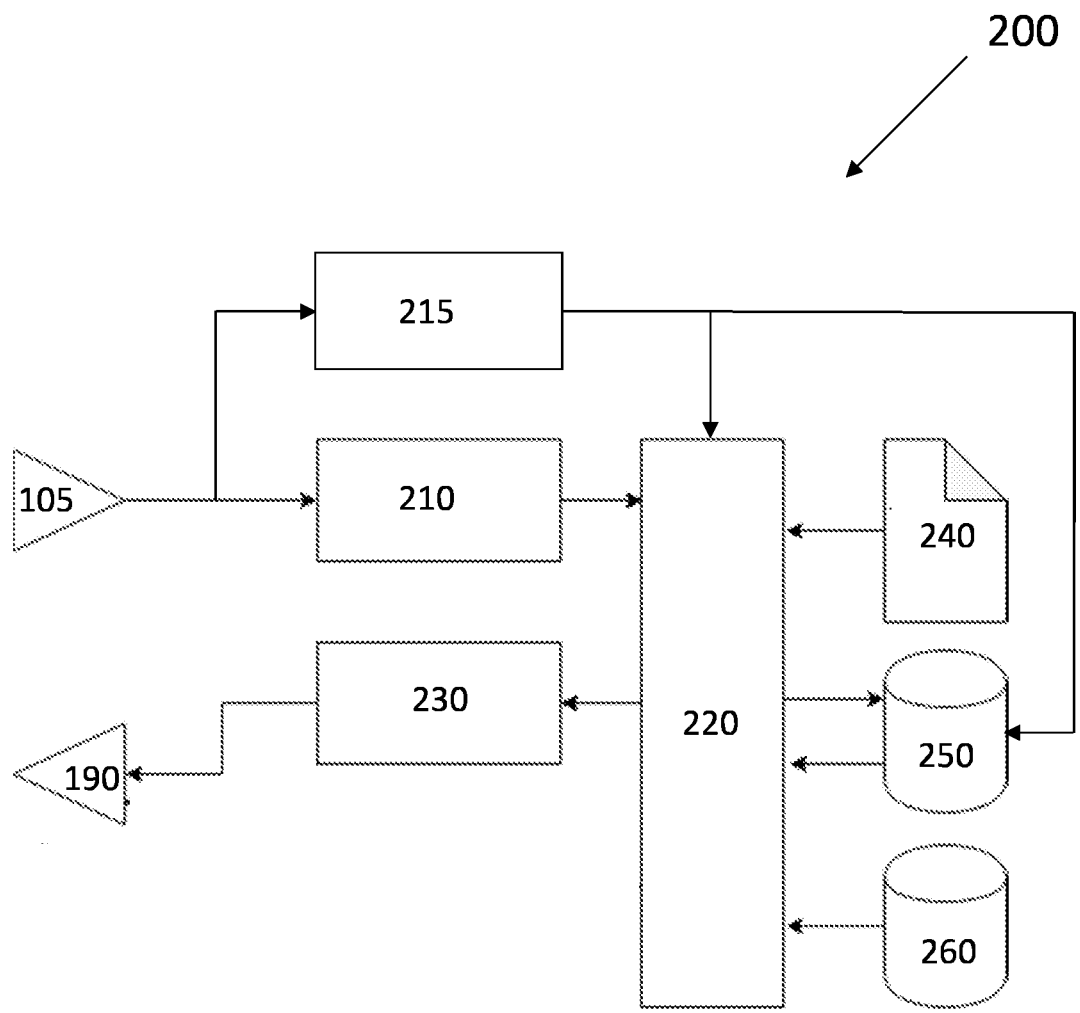
FIG. 8 shows the system shown in FIG. 7 further comprising treatment model module, a dialogue history module and a patient data module.

FIG. 8 shows the system shown in FIG. 7 further comprising a user engagement module 215, a treatment model module 240, a dialogue history module 250 and a patient data module 260.

The user engagement module 215 is configured to determine the user's engagement level. Its purpose is to estimate the likelihood that the user will perform the next expected action, such as providing a second input, for example. More specifically, the user engagement module reviews the input 105, all the previous inputs and some other metadata, such as time between responses, number of app activations over the last week, level of environmental noise at the user's current location. The user engagement module 215 then utilises a statistical method to make a determination of the user's current engagement level. In some embodiments, the statistical method is supplemented by a set of rules. Having determined the user's engagement level, the user engagement module 215 is then configured to provide the user engagement level to the dialogue planning module 220 for use in determining the output 190. The user engagement module 215 is also configured to provide the user engagement level to the dialogue history module 250.

The treatment model module 240 is configured to provide a computer-readable representation of a treatment protocol to the dialogue planning module 220, wherein the treatment protocol is a series of steps for improving a user's state of wellbeing. The treatment protocol is determined based, at least in part, on the input and is based on the obtained user data and/or data obtained during clinical assessment. The treatment model module 240 is configured to provide the treatment protocol to the dialogue planning module 220 for use in determining the output 190.

The dialogue history module 250 is configured to store previous inputs and previous outputs. The previous input is associated with a corresponding event, wherein the event comprises the previous input, a previous output and, where present, a second input. In some embodiments, the user engagement level is predicted, at least on part, based on a previous event. More preferably, the user engagement level is determined based on a plurality of previous events, wherein the plurality of previous events correspond to inputs received from a plurality of previous user. For example, the dialogue history module 250 may store previous inputs, output and/or events corresponding to tens, hundreds, thousands or millions of previous users.

The user data module 260 is configured to store information about the user. For example, the user data module may comprise the user's name, age, contact details, family members, symptoms, intensity of symptoms, triggers and/or frequency of input, to name a few. However, the previous list is non-exhaustive. Any information regarding the user may be stored. In some embodiments, the data stored in the user data module 260 is used, at least in part, to determine the output. For example, the output for a younger user may comprise a game, whereas the corresponding output for an older user may comprise a task. However, the output may be adapted in any suitable or appropriate way based on the user's data.

Figure 9:
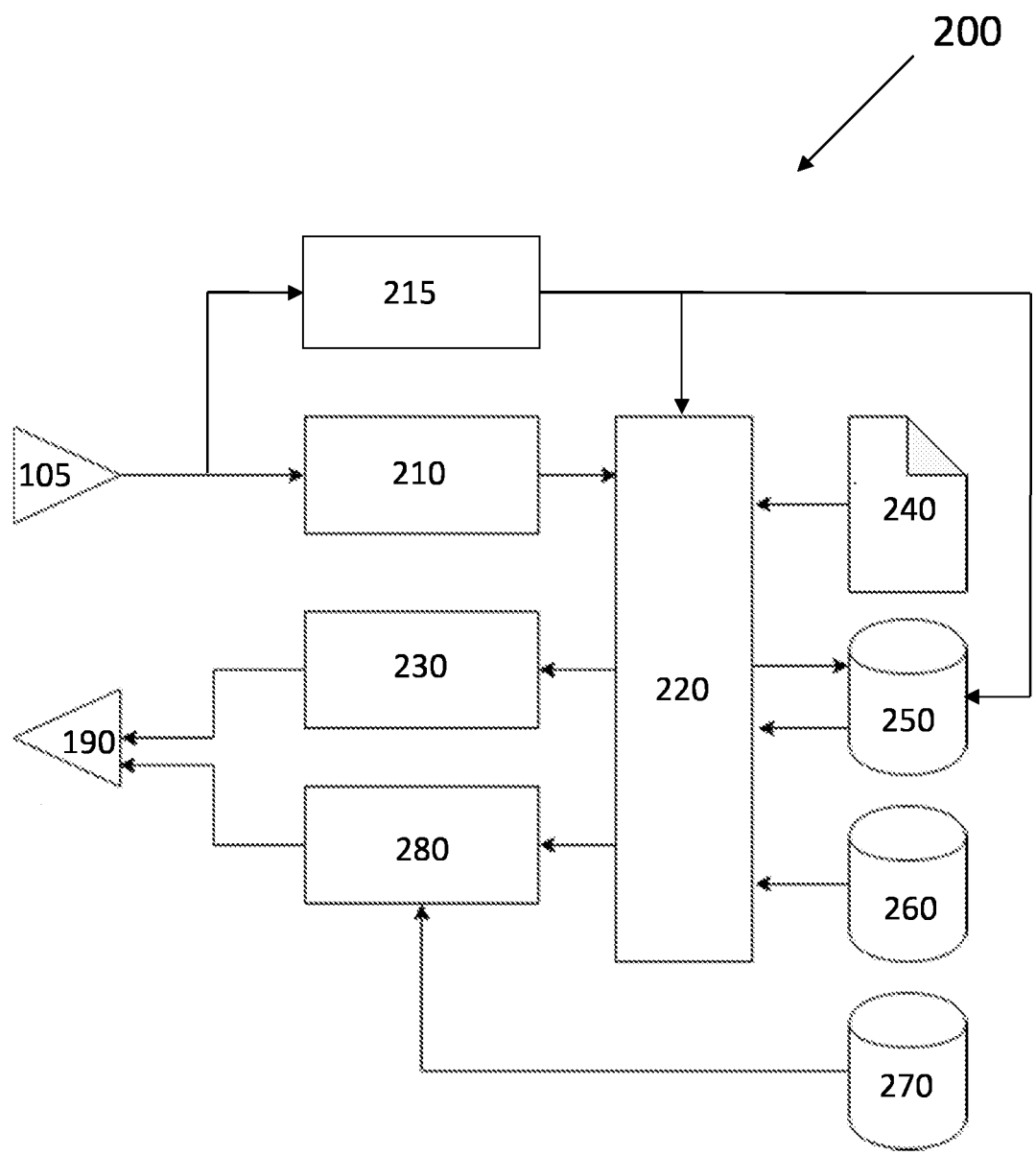
FIG. 9 shows the system shown in FIG. 8 further comprising a content module and a content delivery module.

FIG. 9 shows the system shown in FIG. 8 further comprising a content module 270 and a content delivery module 280.

The content module 270 is configured to store audio and/or visual data. Moreover, the content module 270 is configured to store predefined data for providing to the user. The predefined data may comprise videos, games and/or documents. In some embodiments, the content module 270 also comprises a plurality of phrases, words or stylistic features that correspond to a given human care provider.

Consequently, the output 190 can be adapted to replicated the response of a given human care provider.

The content delivery module 280 is configured to receive data from the content module 270 and generate an output 190. Therefore, in some embodiments, the output 190 comprises data from the natural language generation module 230 and the content delivery module 280.

For example, a user's input may comprise "good morning", to which the computer may assign the intent 'greeting', with no slots. Alternatively, or in addition, a user's input may comprise "I feel like I am letting everyone down by not being able to go out", to which the computer may assign the intent 'inform_thought', with the slot value 'thought_self_blame'.

Table 1, below, shows a series of potential inputs and their corresponding intents and, where present, slots. The inputs shown in Table 1 may be received from a user subjected to "Vicious cycle" activity, wherein "Vicious cycle" activity is a form of CBT formulation. The purpose of the "Vicious cycle" activity is to explain the relationships between thoughts, physical sensations, emotions, and behaviours. The key message conveyed to a user is that each of their thoughts, physical sensations, emotions, and behaviours can reinforce each other in a vicious cycle which leads to increased and sustained anxiety. The present invention may be used to assist a user with breaking this cycle.

Alternatively, or in addition, a slot may be: thought_self_conscious; thought_catastrophising; thought_others_wellbeing; thought_own_wellbeing; thought_getting_things_done; sensation_shaking; sensation_chest_problems; sensation_difficulty_concentrating; sensation_sweating; sensation_tiredness; sensation_flushes; sensation_breathing_difficulties; emotion_anger; emotion_guilt; emotion_frustration; behaviour_checking; behaviour_overplanning; behaviour_suppression; behaviour_reassurance; and/or behaviour_medication, for example.

However, various further aspects and embodiments of the present invention will be apparent to those skilled in the art in view of the present disclosure. Accordingly, the provided examples are exemplary only and are not limiting.

Figure 10:
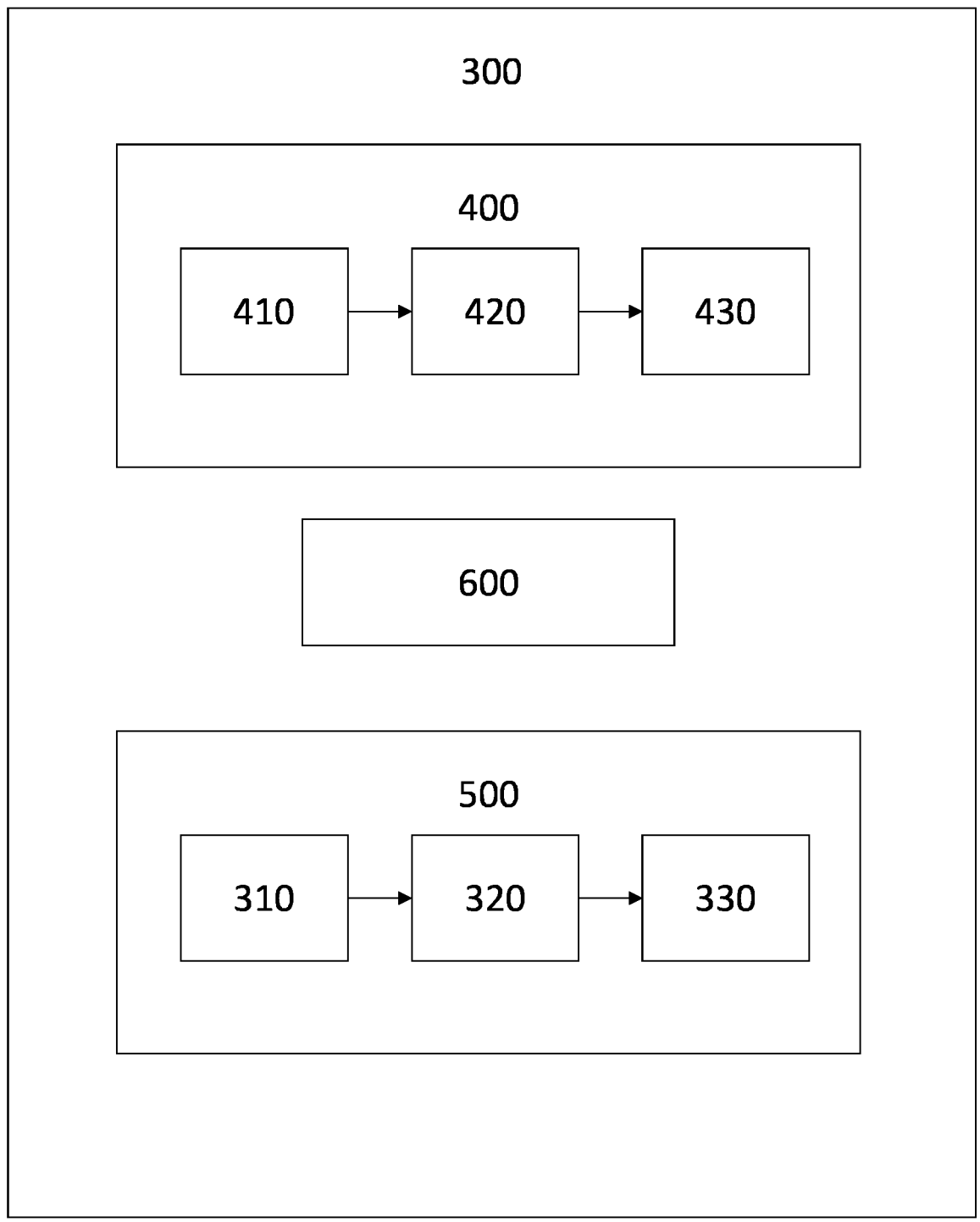
FIGS. 10 and 11 are a schematic of conversational agent according to some embodiments of the present invention.

FIG. 10 shows a conversational agent 300 comprising an active sub-dialogue unit 400, a background sub-dialogue unit 500 and an adjudicator 600. FIG. 10 shows a single background sub-dialogue unit 500 for simplicity. However, any number of background sub-dialogue units may be present within the conversation agent 300.

The active sub-dialogue unit 400 comprises a natural language understanding module 410, a sub-dialogue planning module 420, and an output generation module 430. The active natural language understanding module 410 is configured to receive an input from a user and, if present, within the input, identify an intent from a list of predetermined

TABLE 1 example user inputs and their corresponding intents and, where present, slots.

| Input | Intent | Slots | Description |
|---|---|---|---|
| Yes<br>Of course<br>cool | affirm | None | The user agrees or confirms. |
| no<br>nope<br>none<br>definitely not | deny | None | The user disagrees |
| Goodbye<br>Good night<br>bye | goodbye | None | The user greets the system at the end of a conversation. |
| hi<br>hello<br>hi there | greet | None | The user greets the system at the start of a conversation |
| I feel like I am letting everyone down by not being able to go out. | inform_thought | thought_self_blame | User describes a thought they had |
| I felt completely helpless and lost and had nobody to make decision for me. | inform_thought | thought_not_being_in_control | User describes a thought they had |
| The emotion going through my mind at the time is failure and if someone says that about me it must be true. | inform_thought | thought_inadequacy | User describes a thought they had |
| my heart would be faster and I'd feel sick and uneasy | inform_sensation | sensation_heart_palpitations sensation_stomach_problems | User describes a physical sensation |
| I just notice that I'm really tense | inform_sensation | sensation_muscle_tension | User describes a physical sensation |
| When it's bad I get a racing heart | inform_sensation | sensation_heart_palpitations | User describes a physical sensation |
| Fear and anxiety about what might happen | inform_emotion | emotion_fear emotion_anxiety | User describes an emotion they felt |
| Which in turn leads me to feel terrible | inform_emotion | emotion_sadness | User describes an emotion they felt |
| I felt disheartened and maybe a bit let down | inform_emotion | emotion_sadness | User describes an emotion they felt |
| I often go onto my phone and check social media | inform_behaviour | behaviour_distraction | User describes a behaviour they engaged in |
| I thought about skipping work and going somewhere so I could be alone | inform_behaviour | behaviour_avoidance | User describes a behaviour they engaged in |
| I was a little short tempered with my daughter. | inform_behaviour | behaviour_aggression | User describes a behaviour they engaged in | intents associated with the active sub-dialogue unit 400. The predetermined list of intents for each sub-dialogue unit comprises between six and ten intents in most embodiments. It would be unusual for the number of intents on the predetermined list to exceed 20. The sub-dialogue unit will be more accurate and efficient when it works with a smaller number of intents. The active sub-dialogue planning module 420 is configured to determine an output based, at least in part, on the identified intent from the list of predetermined intents associated with the active sub-dialogue unit 400. The active output generation module 430 is configured to provide the output to the user.

Similarly, the background sub-dialogue unit 500 comprises a natural language understanding module 510, a sub-dialogue planning module 520, and an output generation module 530. The background natural language understanding module 510 is configured to receive an input from a user and, if present within the input, identify an intent from a list of predetermined intents associated with the background sub-dialogue unit 500. The background sub-dialogue planning module 520 is configured to determine an output based, at least in part, on the identified intent from the list of predetermined intents associated with the background sub-dialogue unit 500. The background output generation module 530 is configured to provide the output, where appropriate, to the user.

The adjudicator 600 is configured to identify each sub-dialogue unit comprising a natural language understanding module that identifies an intent; determine which one of the identified sub-dialogue units meets a predetermined criterion; and select the sub-dialogue unit that meets the predetermined criterion such that only the selected sub-dialogue unit determines and provides an output to the user in response to each input. One such criterion may be that the sub-dialogue unit has completed its delivery of its element of care and therefore control of the conversation should be handed back to the orchestrator.

Figure 11:
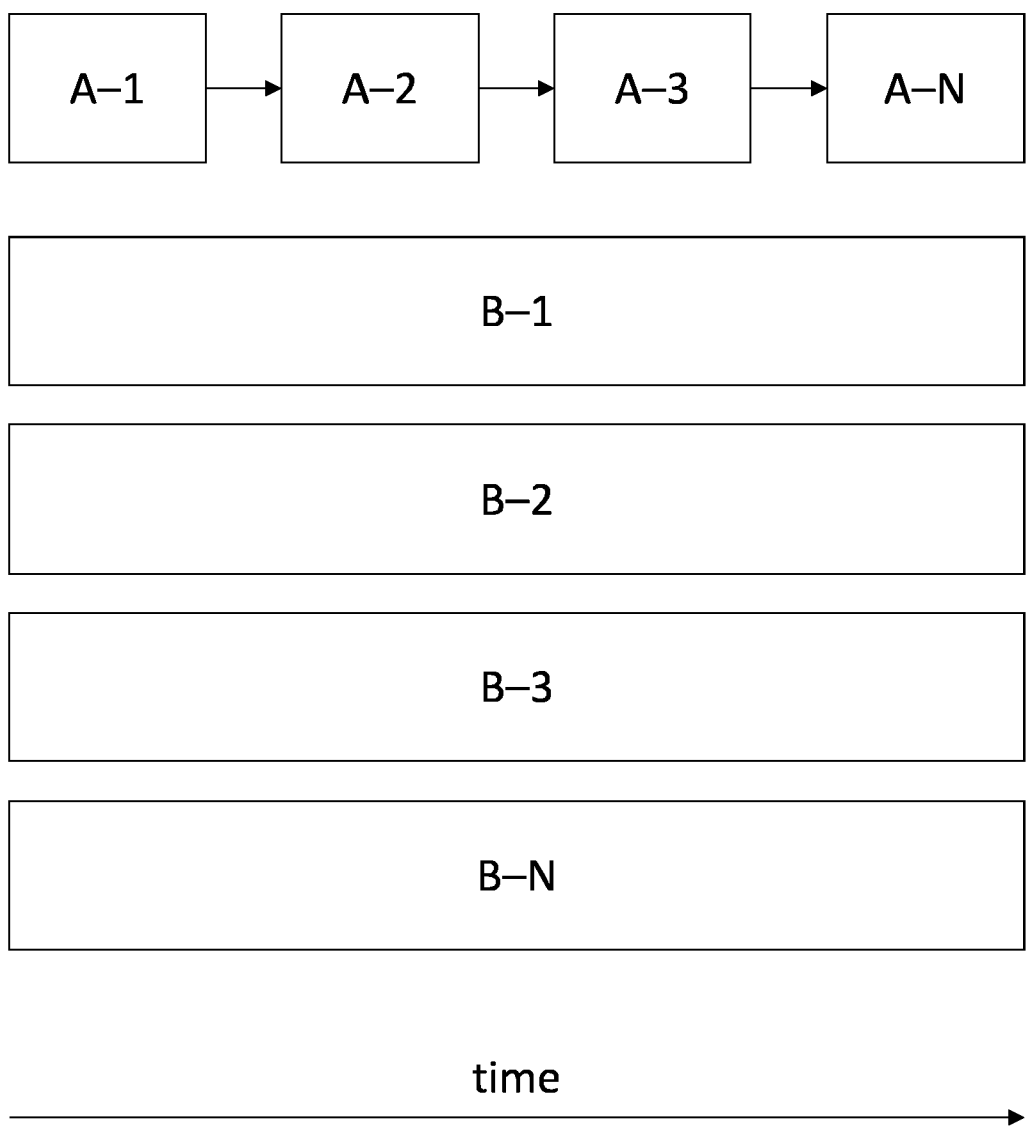

FIG. 11 shows a conversational agent, in use, wherein the conversation agent comprises a plurality of sub-dialogue units, A-1 to A-N, and a plurality of background sub-dialogue units, B-1 to B-N. Any number of sub-dialogue units and/or background sub-dialogue units may be used. As shown, each sub-dialogue unit, A-1 to A-N, is configured to act in series. Therefore, a subsequent sub-dialogue unit A-2 is only able to gain control of the conversation when a previous sub-dialogue A-1 has finished. Therefore, no more than one sub-dialogue unit, A-1 to A-N, receives each input.

Conversely, each background sub-dialogue unit, B-1 to B-N, is configured to act in parallel with each other and the series of sub-dialogue units A-1 to A-N. Therefore, each background sub-dialogue units, B-1 to B-N, receives each input.

For example, a conversation may result in a plurality of sub-dialogue units being activated in series, with the orchestrator being activated briefly between each of the sub-dialogues that are configured to provide an element of care. Meanwhile, each background sub-dialogue unit receives each input from the user. However, a background sub-dialogue unit is only selected to determine and provide an output to the user if a predetermined criterion is met. If the predetermined criterion is met, the selected background sub-dialogue unit becomes the active sub-dialogue unit.

The natural language understanding module 410, 510; sub-dialogue planning module 420, 520; and output generation module 430, 530 of each sub-dialogue unit 400, 500 may be the natural language understanding module 210; dialogue planning module 220; and natural language generation module 230 of the system 200.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example, with reference to several embodiments, it is not limited to the disclosed embodiments. Alternative embodiments could be constructed without departing from the scope of the invention as defined in the appended claims.

The invention claimed is:

1. A computer-based system comprising a conversational agent for maintaining or improving the wellbeing of a user presenting with mental health needs by the delivery of a psychotherapy protocol, the conversational agent comprising:
   a plurality of treatment sub-dialogue units, each configured to deliver an element of the psychotherapy protocol;
   an orchestrator configured to present the treatment sub-dialogue units to the user, sequentially; and
   a risk assessment sub-dialogue unit configured to run in parallel to an active sub-dialogue unit with which the user is engaged;
   wherein each sub-dialogue unit and the orchestrator comprises:
      a natural language understanding module configured to receive at least one of an input from the user and a reply from the user and determine an intent and, where present, a slot within the at least one of an input and a reply;
      a dialogue planning module configured to determine an output based, at least in part, on the at least one of the intent and the slot associated within the at least one of an input and a reply, and
      an output generation module configured to provide the output to the user;
   wherein the dialogue planning module of each treatment sub-dialogue unit is further configured to determine its output based, at least in part, on the element of the psychotherapy protocol being delivered to the user; and
   wherein the risk assessment sub-dialogue unit comprises a natural language understanding module configured to receive the at least one input and reply from the user, and analyse the at least one input and reply to determine, if present within the at least one input and reply, at least one intent indicating a risk and, where present, at least one slot within the at least one input and reply; and
   wherein the risk assessment sub-dialogue unit is configured to, when the at least one intent indicating the risk is present, take an action based, at least on part, on the identified risk.

2. The computer-based system according to claim 1, wherein the psychotherapy protocol is a transdiagnostic CBT protocol.

3. The computer-based system according to claim 1, wherein the orchestrator is configured to select which treatment sub-dialogue unit is presented to the user.

4. The conversational agent according to claim 1, wherein the risk assessment sub-dialogue unit is configured to receive and analyse all inputs and replies from the user, wherein the risk assessment sub-dialogue unit further comprises a dialogue planning module configured to determine an output based, at least in part, on at least one of the intent and the slot associated within the at least one of an input and a reply, and an output generation module configured to provide the output to the user.

5. The computer-based system according to claim 1, wherein the conversational agent further comprises an adjudicator configured to identify each sub-dialogue unit comprising a natural language understanding module that identifies an intent; determine which of the identified sub-dialogue units meets a predetermined criterion; and select the sub-dialogue unit that meets the predetermined criterion such that only the selected sub-dialogue unit determines and provides an output to the user in response to at least one of each input and each reply.

6. The computer-based system according to claim 5, wherein the adjudicator is configured to enable the risk assessment sub-dialogue unit to provide the output to the user, where an intent relating to risk is identified.

7. The computer-based system according to claim 1, and a treatment model module configured to provide a computer-readable representation of a psychotherapy protocol.

8. The system according to claim 7, further comprising a dialogue history module configured to store previous inputs, outputs and, where present, replies; and further comprising a user data module configured to store information about the user.

9. The system according to claim 7, further comprising a content module configured to store predefined data for providing to the user.

10. A computer-implemented method for maintaining or improving the wellbeing of a user presenting with mental health needs by the delivery of a psychotherapy protocol, the method comprising:
receiving an input from a user at an orchestrator;
analysing, by the orchestrator, the input using a natural language understanding module configured to determine an intent and, where present, a slot within the input;
selecting, by the orchestrator, a treatment sub-dialogue unit configured to deliver an element of the psychotherapy protocol and presenting the selected sub-dialogue unit to the user;
analysing, by the selected treatment sub-dialogue unit, the input using a natural language understanding module configured to determine at least one intent and, where present, at least one slot within the input;
analysing, by a risk assessment sub-dialogue unit, the input using a natural language understanding module configured to determine at least one intent indicating a risk and, where present, at least one slot within the input, wherein the risk assessment sub-dialogue unit is configured to run in parallel to the selected sub-dialogue unit, and wherein the risk assessment sub-dialogue unit is configured to, when the at least one intent indicating the risk is present, take an action based, at least on part, on the identified risk;
determining an output using a dialogue planning module of the selected treatment sub-dialogue unit, wherein the output is based, at least in part, on the element of the psychotherapy protocol being delivered to the user and on the at least one intent and slot associated with the input;
providing the output to the user using an output generation module of the selected treatment sub-dialogue unit;
receiving, in response to the output, a reply from the user;
analysing the reply using a natural language understanding module of the selected treatment sub-dialogue unit, wherein the natural language understanding module is configured to determine at least one intent and, where present, at least one slot within the reply;
determining a subsequent output using the dialogue planning module of the selected treatment sub-dialogue unit, wherein the dialogue planning module is configured to determine the subsequent output based, at least in part, on the element of the psychotherapy protocol being delivered to the user and the at least one intent and slot associated with the reply; and
providing the subsequent output to the user using the output generation module of the selected treatment sub-dialogue unit.

11. The method according to claim 10, further comprising:
determining a user engagement level, wherein the subsequent output is based, at least in part, on the user engagement level; further comprising:
determining if the user engagement level is below a predetermined threshold; and
sending an alert to a second user upon determining a user engagement level below the predetermined threshold.

12. The method according to claim 11, wherein after having received the alert, the second user provides at least one of a second output to the user and an amendment to the subsequent output determined by the dialogue planning module of the selected treatment sub-dialogue unit, wherein the second output and/or amended output is configured to increase and/or maintain the user engagement level above the predetermined threshold.

13. The method according to claim 12, further comprising:
reviewing, using the natural language understanding module, the at least one second output and amended output and providing, using the dialogue planning module of the selected treatment sub-dialogue unit, further amendments to the at least one second output and amended output.

14. The method according to claim 10, further comprising:
reviewing a memory configured to store at least one event, wherein each event comprises:
an intent and, where present, a slot corresponding to a previous input;
a previous output corresponding to the previous input, and
where present, a previous reply received in response to the previous output, wherein the output is based, at least in part, on an event stored within the memory.

15. The method according to claim 10, wherein the at least one output is based, at least in part, on at least one of:
the need to obtain a piece of information from the user;
the piece of information required next from the user;
a question contained within the input or reply;
the frequency of questions contained within the input or reply;
the frequency of questions generated by the natural language generation module;
the amount of repetition within an input or reply compared to a previous input or reply; and the amount of repetition within an output compared to a previous output.

16. The method according to claim 10, wherein the method further comprises: alerting a second user in response to at least one of:
- determining when the at least one of an input and a reply is outside of the psychotherapy protocol; and
- determining when the natural language understanding module is unable to determine the intent or, where present, slot associated with the input.

* * * * *

UNITED STATES PATENT AND TRADEMARK OFFICE
CERTIFICATE OF CORRECTION

| | | |
|---|---|---|
| PATENT NO. | : 12,293,819 B2 | Page 1 of 1 |
| APPLICATION NO. | : 17/995913 | |
| DATED | : May 6, 2025 | |
| INVENTOR(S) | : Andrew Blackwell et al. | |

It is certified that error appears in the above-identified patent and that said Letters Patent is hereby corrected as shown below:

On the Title Page

In Column 1, item (72), Inventors, Line 2, delete "Danah Tangen," and insert -- Danah Barbara Tangen --, therefor.

In the Claims

In Column 33, Line 1, Claim 4, delete "The conversational agent" and insert -- The computer-based system --, therefor.

In Column 33, Line 27, Claim 8, delete "The system" and insert -- The computer-based system --, therefor.

In Column 33, Line 32, Claim 9, delete "The system" and insert -- The computer-based system --, therefor.

Signed and Sealed this
Fourteenth Day of October, 2025

John A. Squires
*Director of the United States Patent and Trademark Office*